US010010587B2

(12) United States Patent
Addepalli et al.

(10) Patent No.: US 10,010,587 B2
(45) Date of Patent: Jul. 3, 2018

(54) IL-2Rβ-SELECTIVE AGONISTS IN COMBINATION WITH AN ANTI-CTLA-4 ANTIBODY OR AN ANTI-PD-1 ANTIBODY

(71) Applicants: Nektar Therapeutics, San Francisco, CA (US); NEKTAR THERAPEUTICS (INDIA) PVT. LTD., Andhra Pradesh (IN)

(72) Inventors: Murali Krishna Addepalli, Secunderabad (IN); Deborah H. Charych, Albany, CA (US); Seema Kantak, Pacifica, CA (US); Steven Robert Lee, San Leandro, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 15/120,214

(22) PCT Filed: Feb. 20, 2015

(86) PCT No.: PCT/IN2015/000099
§ 371 (c)(1),
(2) Date: Oct. 4, 2016

(87) PCT Pub. No.: WO2015/125159
PCT Pub. Date: Aug. 27, 2015

(65) Prior Publication Data
US 2017/0128539 A1 May 11, 2017

(30) Foreign Application Priority Data

Feb. 21, 2014 (IN) .............................. 499/DEL/2014
Oct. 29, 2014 (IN) ........................... 3087/DEL/2014

(51) Int. Cl.
*A61K 38/20* (2006.01)
*A61K 39/395* (2006.01)
*A61K 47/48* (2006.01)
*C07K 16/28* (2006.01)
*C07K 16/30* (2006.01)

(52) U.S. Cl.
CPC .... *A61K 38/2013* (2013.01); *A61K 39/39558* (2013.01); *A61K 47/48215* (2013.01); *C07K 16/2818* (2013.01); *C07K 16/3015* (2013.01); *C07K 16/3046* (2013.01); *C07K 2317/76* (2013.01)

(58) Field of Classification Search
CPC .......... A61K 38/2013; A61K 38/39558; A61K 47/48215
See application file for complete search history.

(56) References Cited

FOREIGN PATENT DOCUMENTS

| WO | WO 2006/121168 A1 | 11/2006 |
| WO | WO 2006/138572 A2 | 12/2006 |
| WO | WO 2012/065086 A1 | 5/2012 |

OTHER PUBLICATIONS

Liparoto et al., "Biosensor analysis of the interleukin-2 receptor complex", Journal of Molecular Recognition, vol. 12, pp. 316-321, (1999).
Theze et al., "Interleukin 2 and its receptors: recent advances and new immunological functions", Review Immunology Today, vol. 17, No. 10, pp. 481-486, (Oct. 1996).
PCT International Search Report and Written Opinion corresponding to PCT Application No. PCT/IN2015/000099 dated Jun. 29, 2015.
PCT International Preliminary Report on Patentability corresponding to PCT Application No. PCT/IN2015/000099 dated Sep. 1, 2016.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005—2006).
NOF Corporation, PEG Derivatives, Phospholipid and Drug Delivery Materials for Pharmaceuticals, 46 pages, Catalogue 2003-1$^{st}$, (Jan. 2003).
NOF Corporation, PEG Derivatives, Phospholipid and Drug Delivery Materials for Pharmaceuticals, 27 pages, Catalogue 2003-2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).

(Continued)

*Primary Examiner* — Prema Mertz
(74) *Attorney, Agent, or Firm* — Susan T. Evans

(57) ABSTRACT

The invention relates to (among other things) method of administering to a patient suffering from a cancer, the method comprising the steps of: (a) an IL-2Rβ-activating amount of a long acting, IL-2Rβ-selective agonist; and (b) a CTLA-4 pathway-inhibiting amount of an anti-CTLA-4 antibody or a PD-1 pathway-inhibiting amount of an anti-PD-1 antibody.

15 Claims, 20 Drawing Sheets

(56) References Cited

OTHER PUBLICATIONS

Quanta Biodesign, Labeling, Modification and Crosslinking Reagents incorporating our unique monodispersed dPEG™ Technology, 31 pages, (Nov. 5, 2004).

Quanta Biodesign, LTD., Leading Innovator, Producer and Provider of Monodisperse Discrete PEG™ (dPEG™) derivatives, (Product Catalog), 26 pages, (Updated: Jul. 18, 2005).

Quanta Biodesign, LTD., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

Cancer Drug Manual® (BC Cancer Agency), Revised Jun. 1, 2013 (developed May 2010), indicating under the entry for aldesleukin, the following: Drug Name: Aldesleukin. Synonyms: Interleukin-2, IL-2; Common Trada Name(S): Proleukin®.

Label for Proleukin®, indicating in the title, Proleukin® (aldesleukin). In several sections throughout the document, Proleukin® is indicated to be synonymous with aldesleukin. Dated 2011 Prometheus Laboratories, REV. Jul. 2012.

Weiss, G., et al., *Clin Cancer Res*; 17(23), Dec. 1, 2011. The first sentence of the Introduction states, "High-dose recombinant interleukin-2 (rIL-2, aldesleukin, Proleukin) was approved by the U.S. Food and Drug Administration in 1993 . . .".

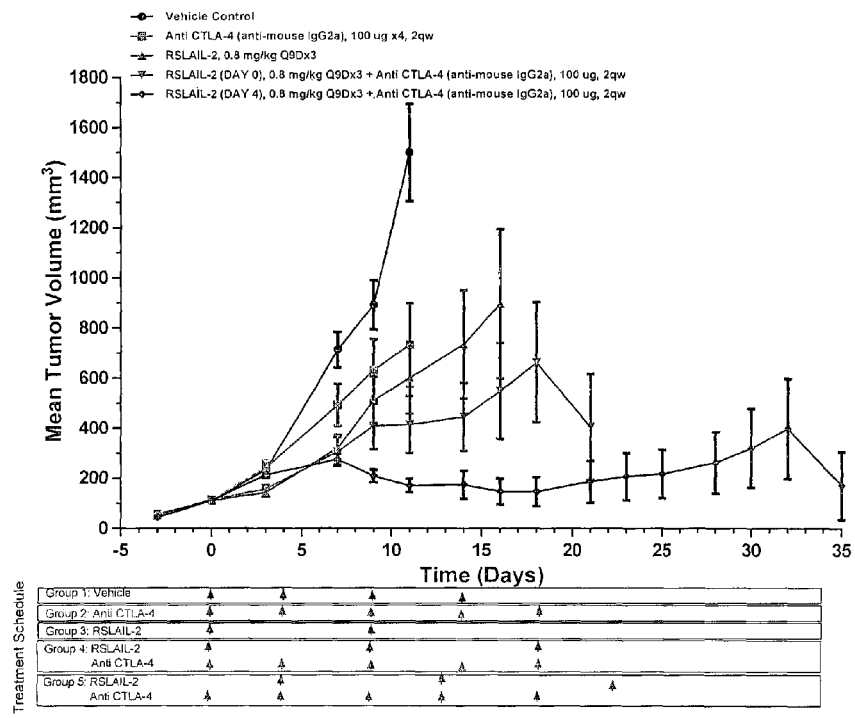
Figure 1: Tumor Volumes (Mean ± SEM)
EVALUATING THE EFFICACY OF RSLAIL-2 IN COMBINATION WITH ANTI-CTLA-4 ANTIBODY ON THE CT26 TUMOR MODEL IN FEMALE BALB/C MICE

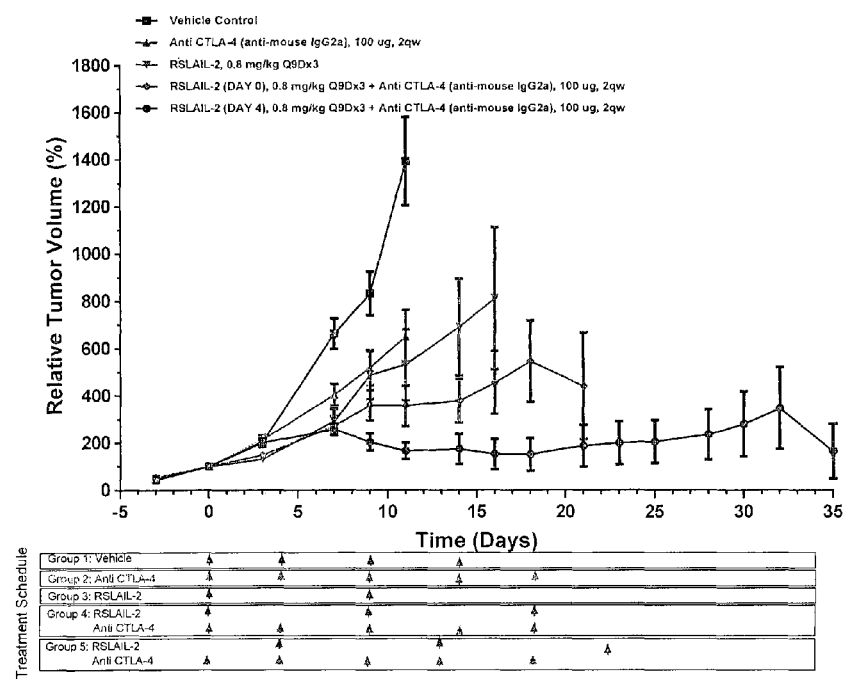
Figure 2: Relative Tumor Volumes (Mean ± SEM)

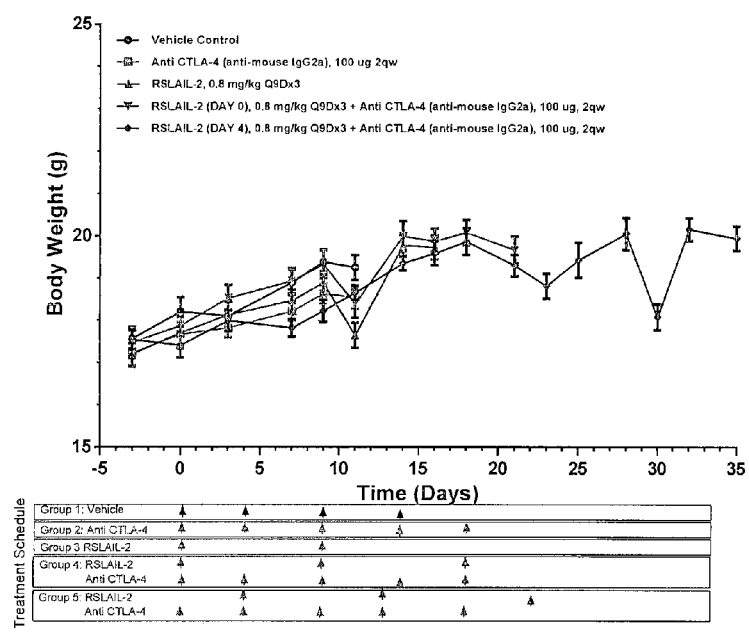
Figure 3: Body Weights (Mean ± SEM)
EVALUATING THE EFFICACY OF RSLAIL-2 IN COMBINATION WITH ANTI-CTLA-4 ANTIBODY ON THE CT26 TUMOR MODEL IN FEMALE BALB/C MICE Figure 4: Tumor Volumes up to Day 30 (Mean ± SEM)
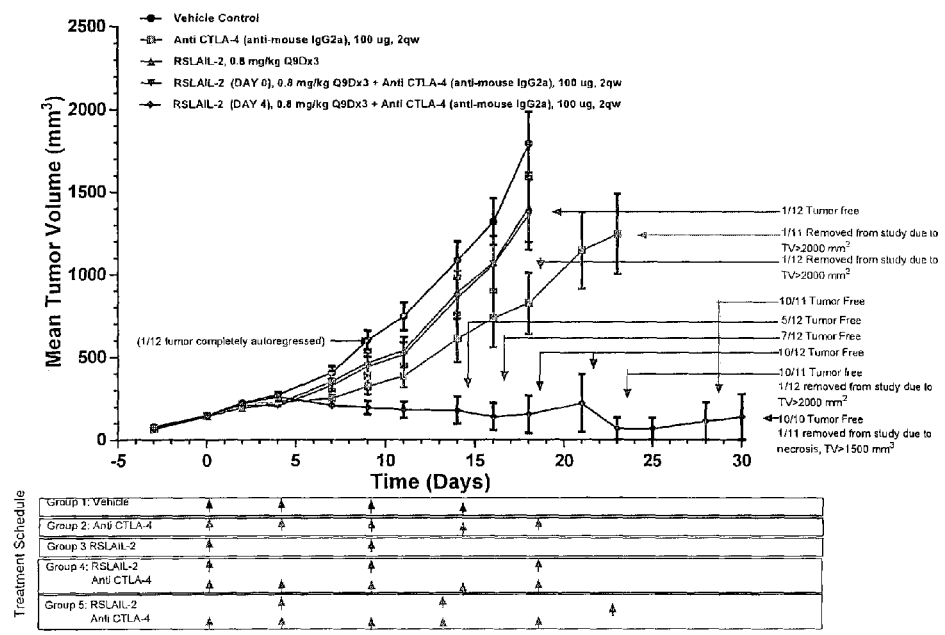

Figure 5: Tumor Volumes up to Day 106 (Mean ± SEM)
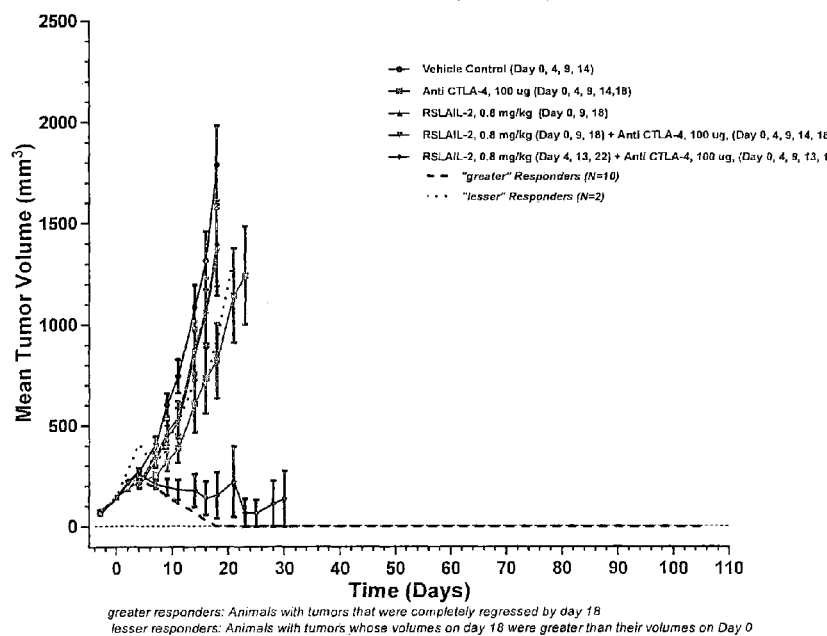

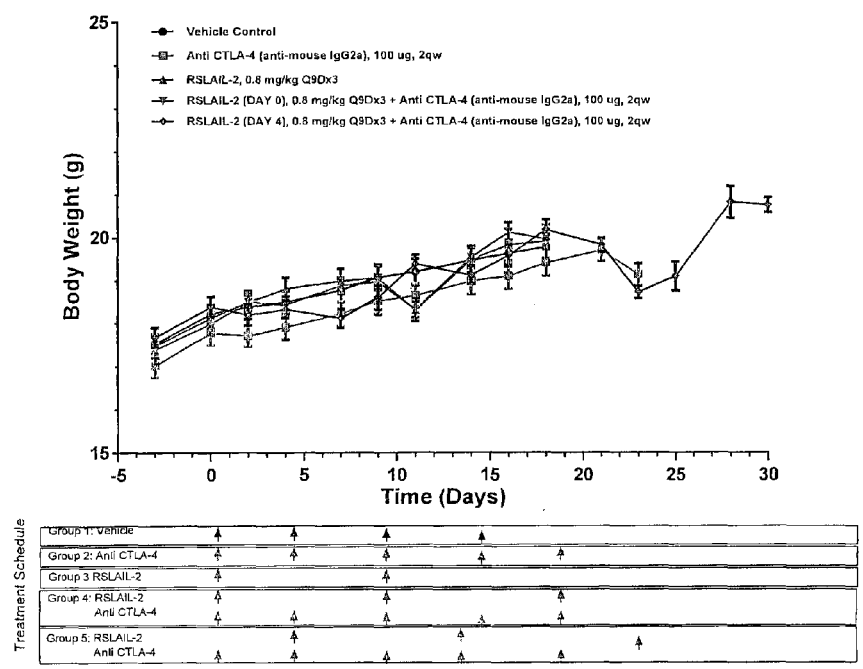
Figure 6: Body Weights (Mean ± SEM)

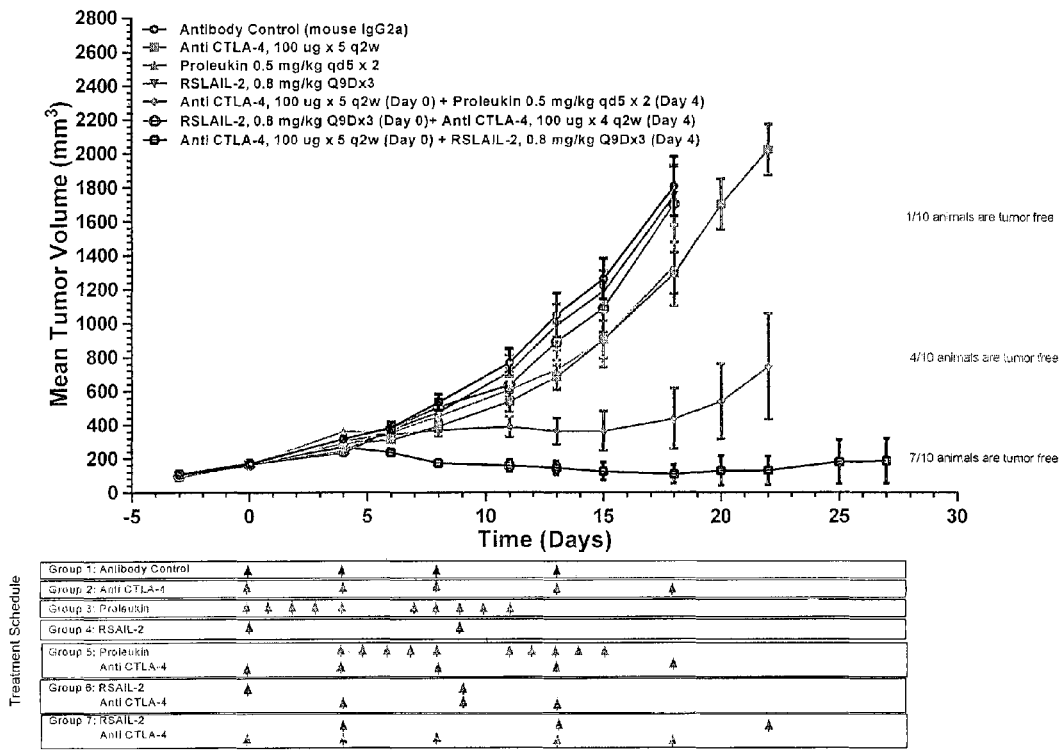
Figure 7: Tumor Volumes to Day 27 (Mean ± SEM)

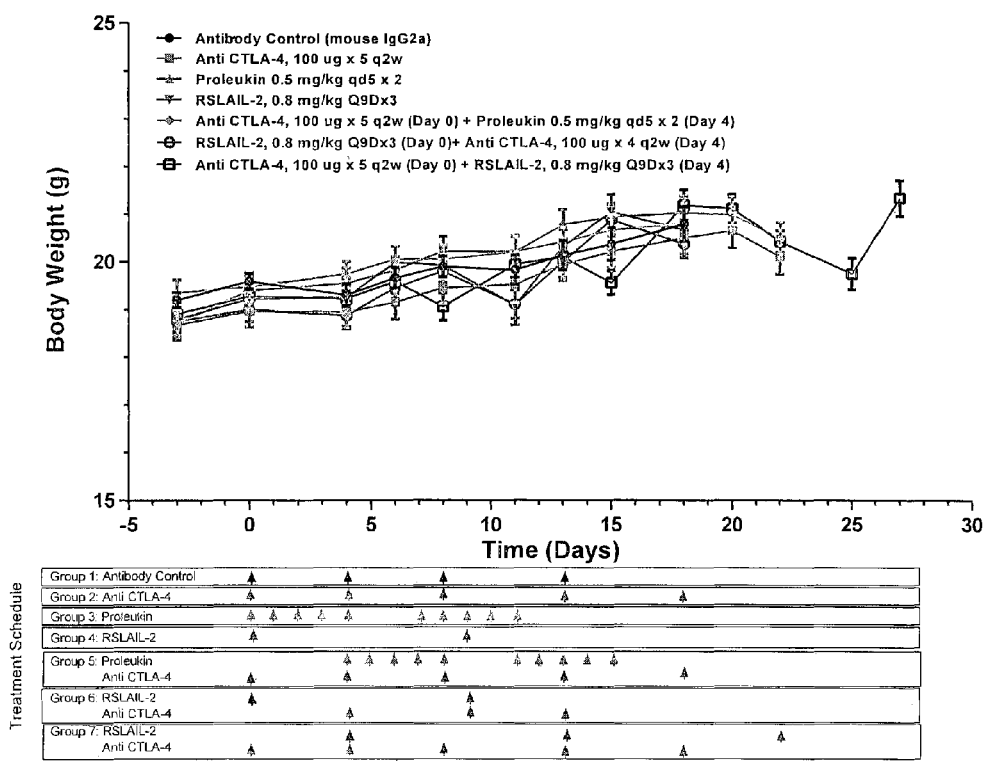
Figure 8: Body Weights to Day 27 (Mean ± SEM)

Figure 9: Tumor Growth to Day 11
EFFICACY STUDY TESTING RSLAIL-2 IN COMBINATION WITH ANTI CTLA-4
ANTIBODY ON THE EMT6 TUMOR MODEL IN FEMALE BALB/C MICE
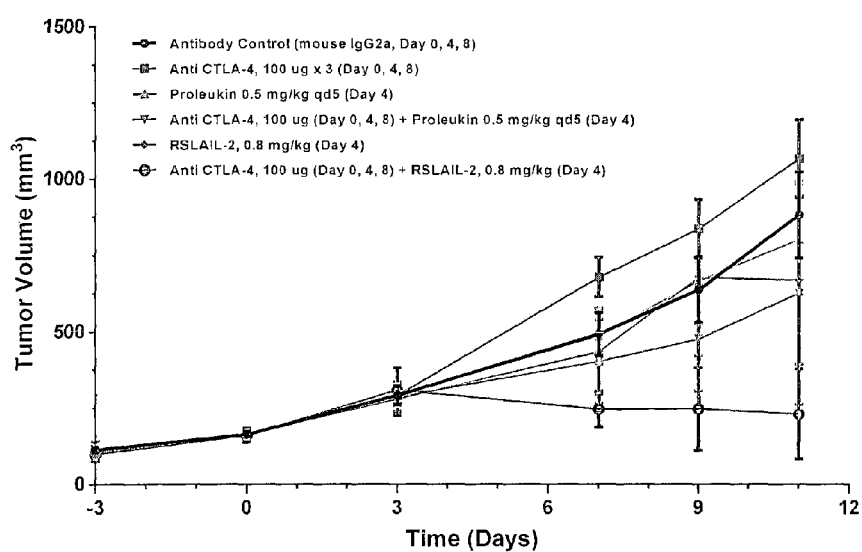

Figure 10: Body Weights and % Changes in Body Weight to Day 11
EFFICACY STUDY TESTING RSLAIL-2 IN COMBINATION WITH ANTI CTLA-4
ANTIBODY ON THE EMT6 TUMOR MODEL IN FEMALE BALB/C MICE
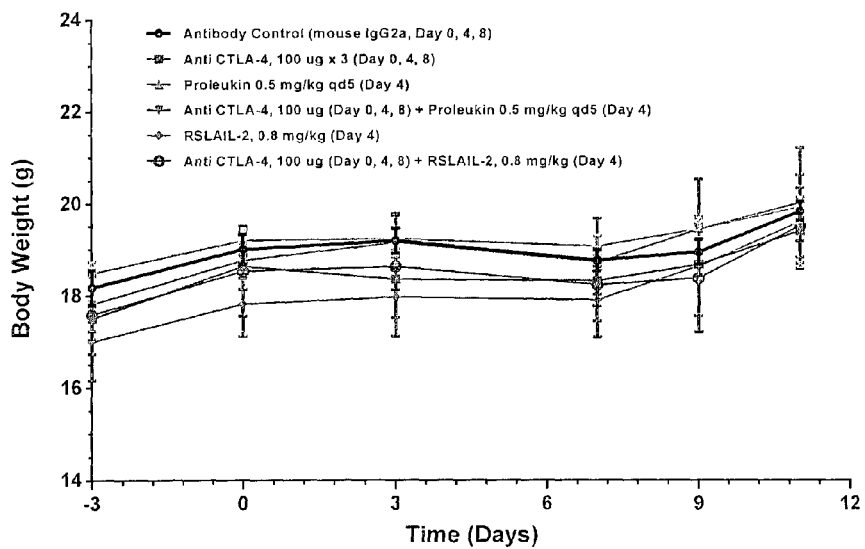

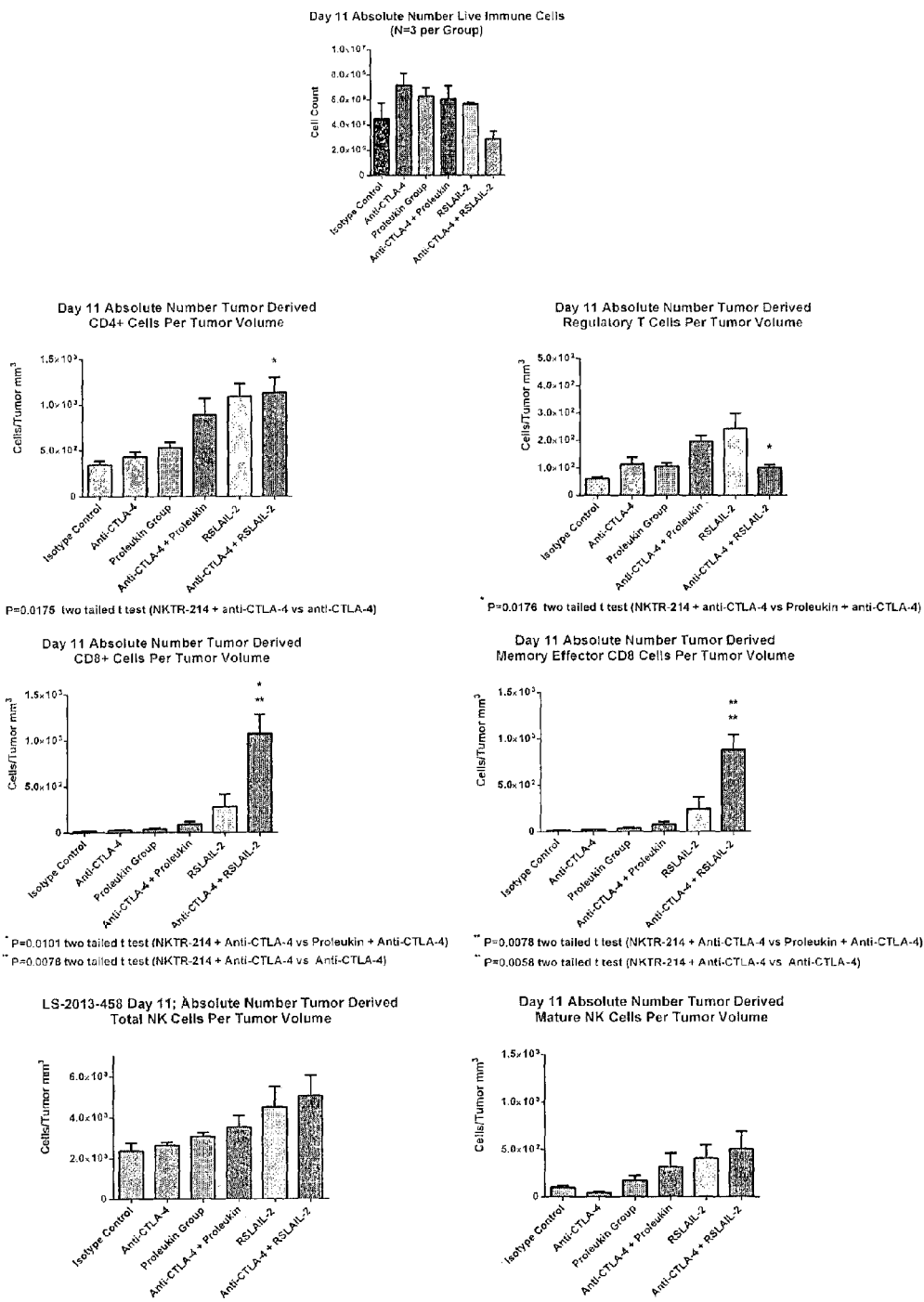
Figure 11: Immune Cell Populations in Tumor on Day 11

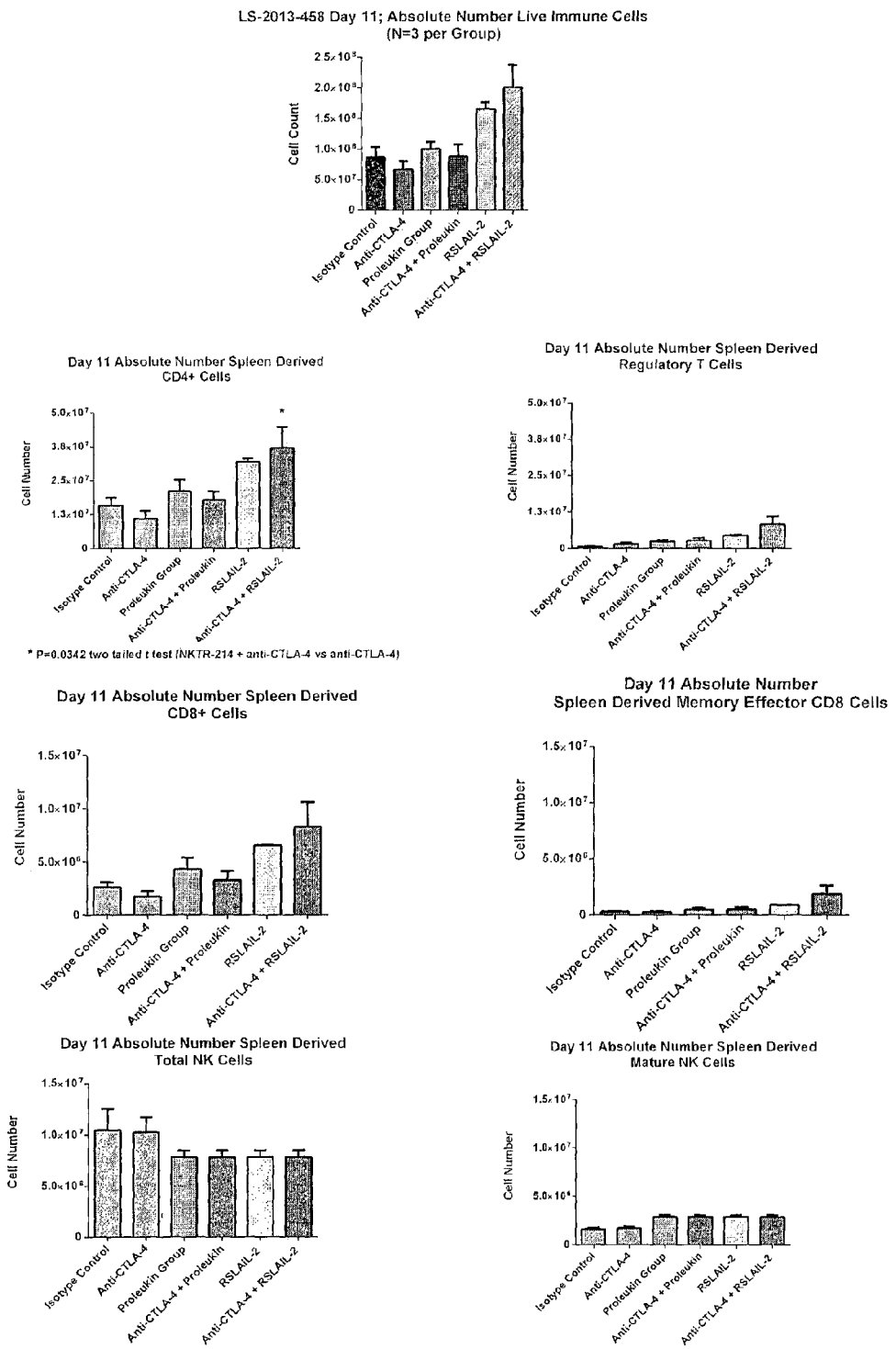
Figure 12: Immune Cell Populations in Spleen on Day 11

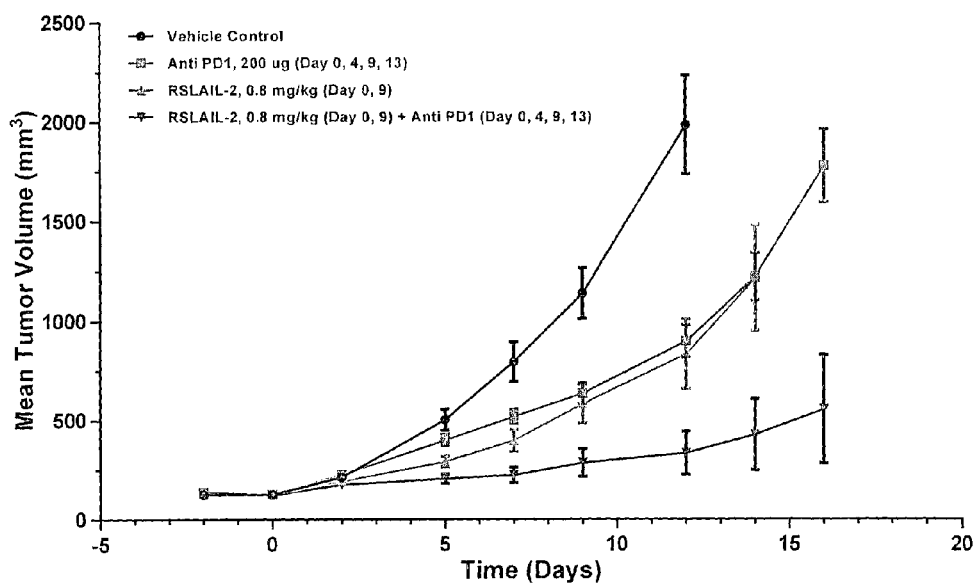
Figure 13: Tumor Volume Data (Mean ± SEM)

Figure 14: Body Weight Data (Mean ± SEM)
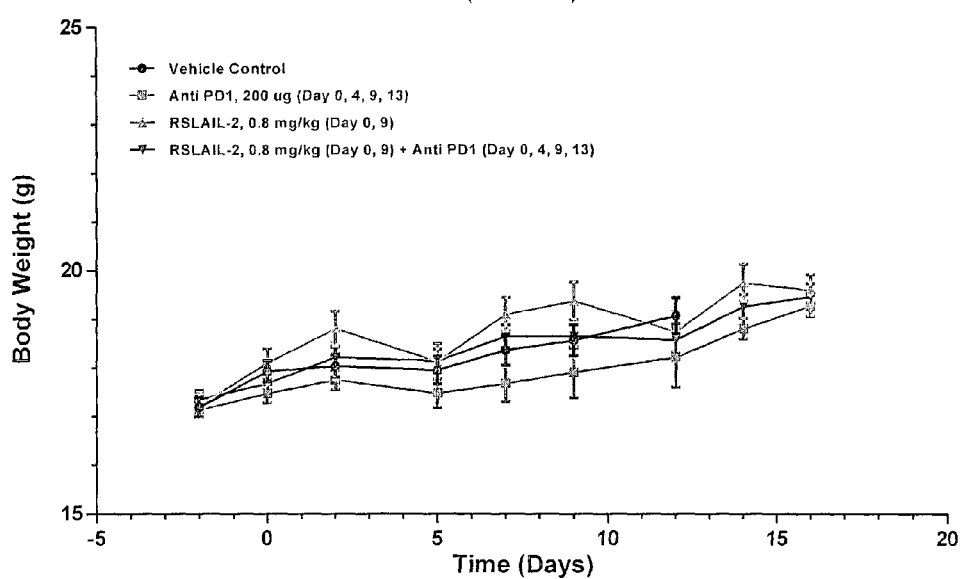

Figure 15: Phase I Tumor Volumes and Body Weights (Mean ± SE)
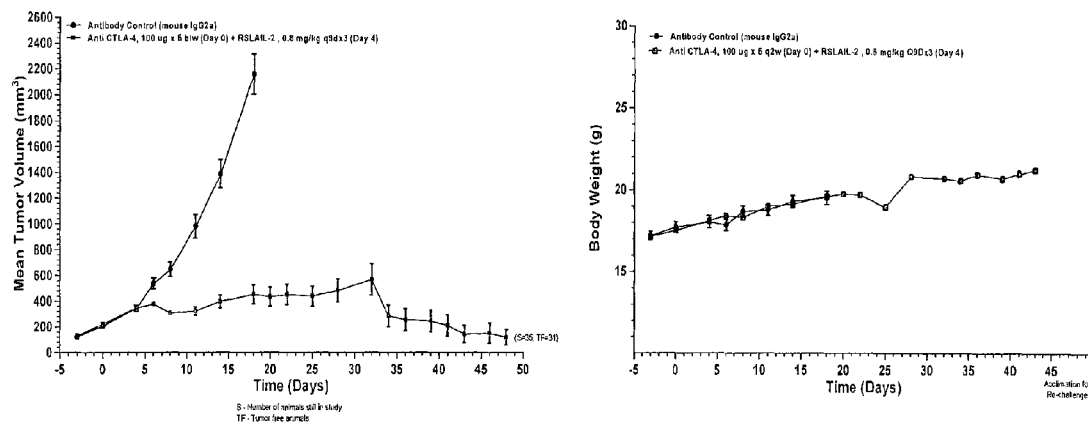
Figure 16: Phase I Relative Tumor Volumes and Body Weight Changes
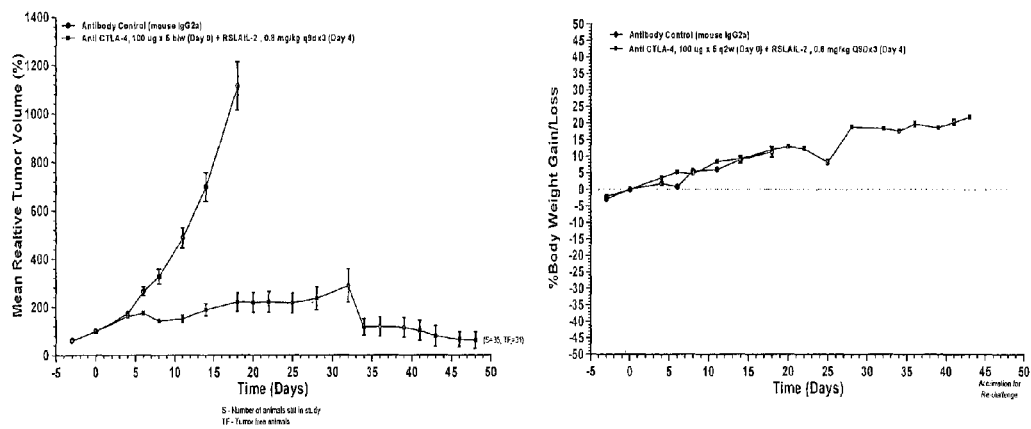

Figure 17: Relative Body Weight Changes
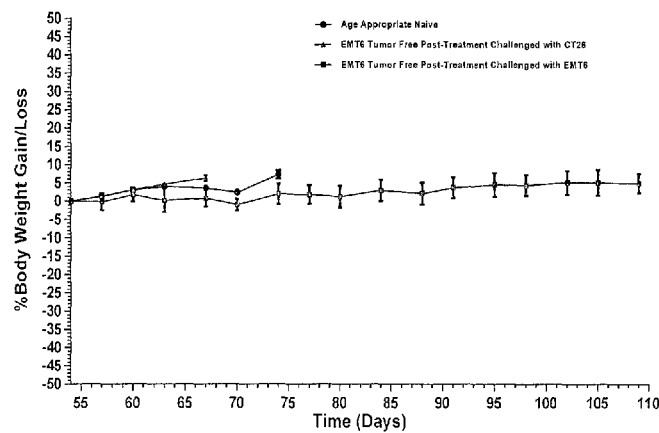
Figure 18: Phase II Tumor Volumes and Body Weights (Mean ± SE)
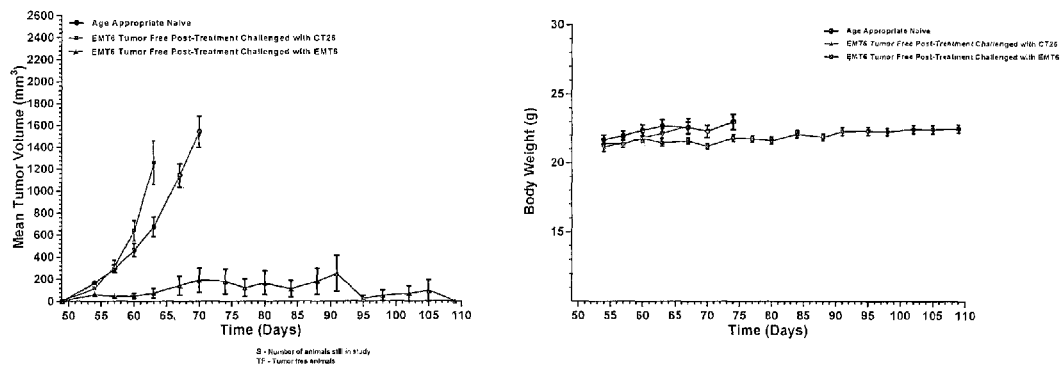

Figure 19: Phase III Summary of Tumor Volumes
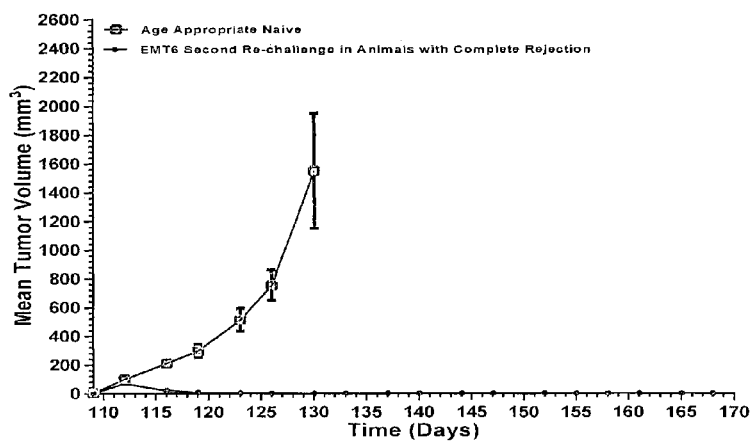
Figure 20: Phase III Summary of Changes in Body Weights
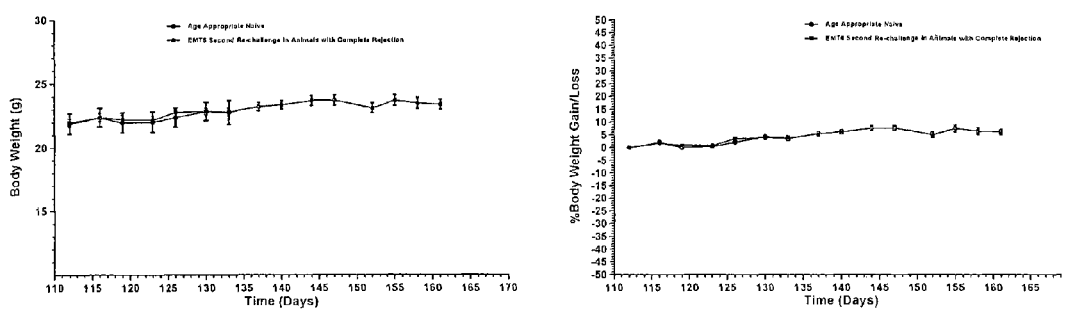

Figure 21: Complete Summary of Tumor Volumes (Day -3 to Day 168)
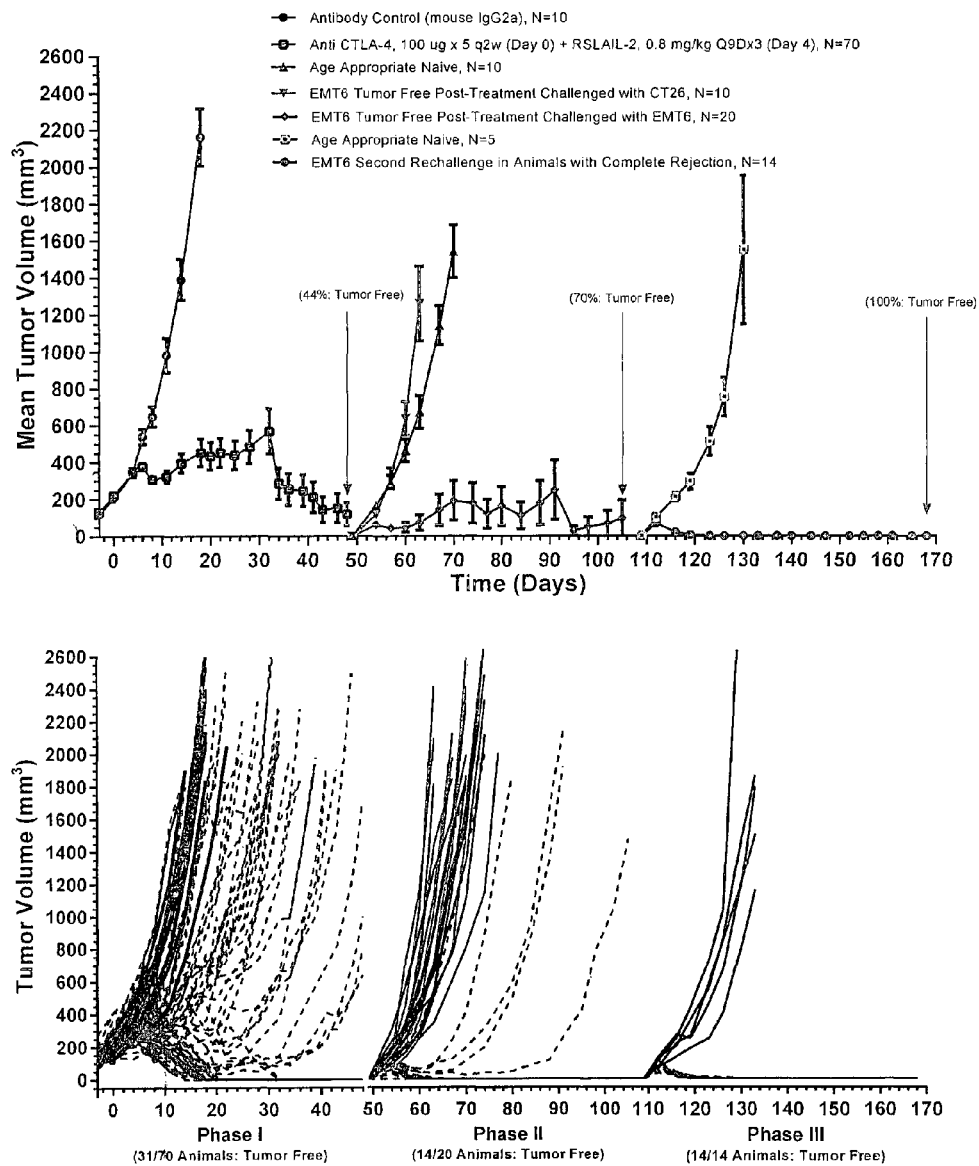

Figure 22: Tumor Volumes and Body Weights, RSLAIL-2 and anti-CTLA-4 combinations (Mean ± SEM)
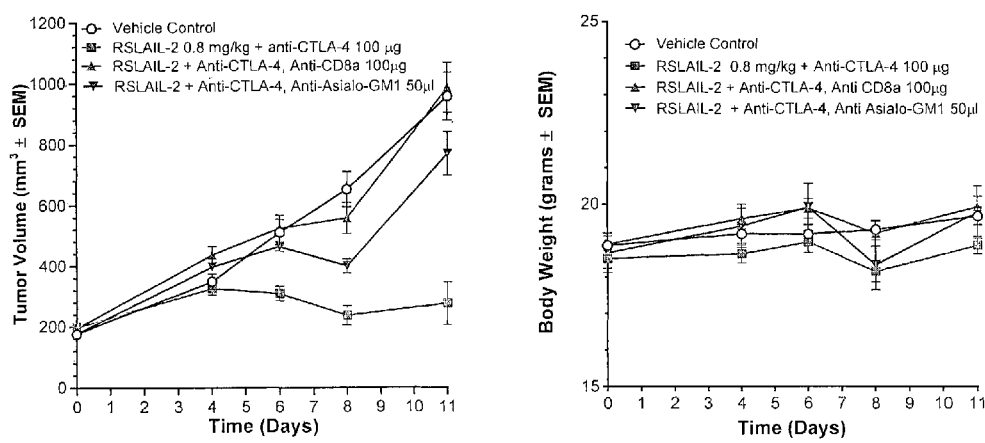
Figure 23: Relative Tumor Volumes and Body Weight Changes, RSLAIL-2 and anti-CTLA-4 combinations
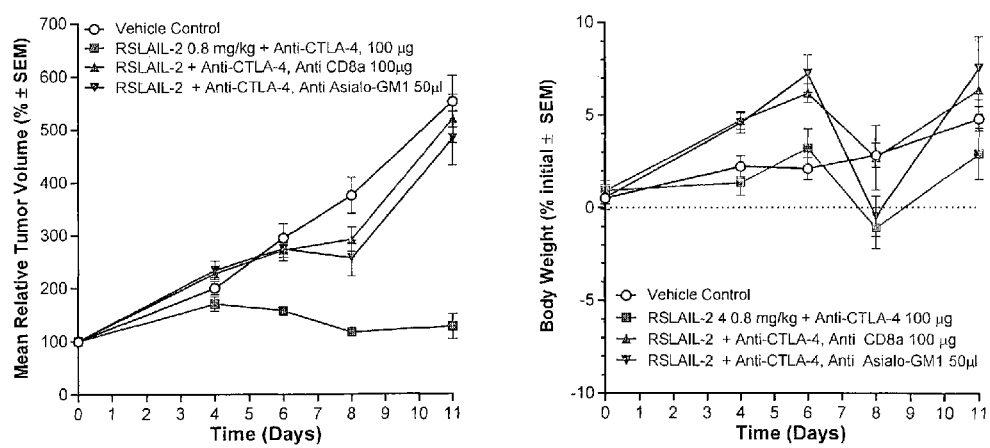

Figure 24: Tumor Volumes and Body Weights, RSLAIL-2 and anti-PD-1 combinations (Mean ± SEM)
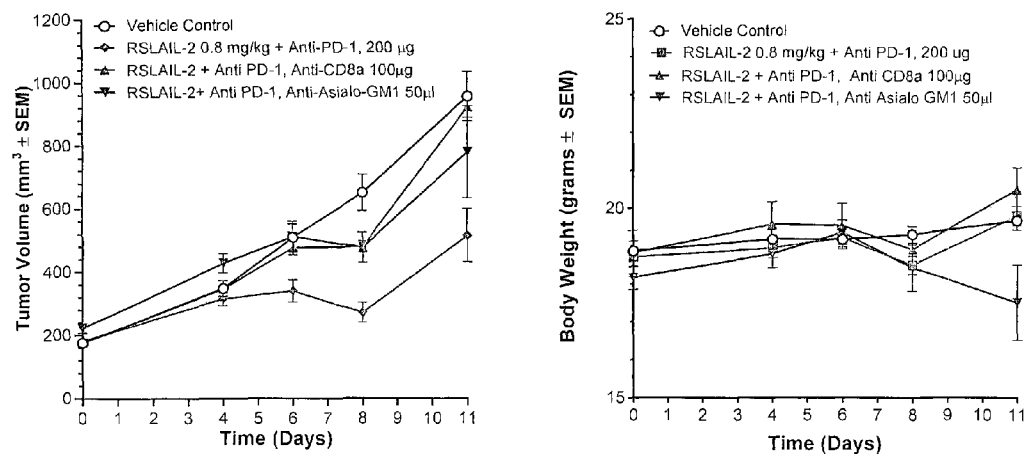
Figure 25: Relative Tumor Volumes and Body Weight Changes, RSLAIL-2 and anti-PD-1 combinations
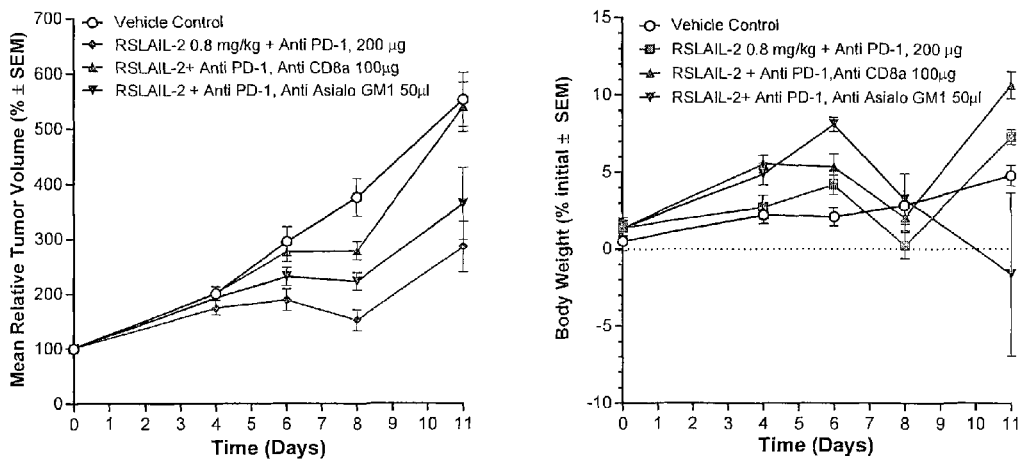

IL-2Rβ-SELECTIVE AGONISTS IN COMBINATION WITH AN ANTI-CTLA-4 ANTIBODY OR AN ANTI-PD-1 ANTIBODY

CROSS REFERENCE TO RELATED APPLICATIONS

This application is a 35 U.S.C. § 371 application of International Application No. PCT/IN2015/000099, filed Feb. 20, 2015, designating the United States, and claims the benefit of priority to Indian Patent Application No. 3087/DEL/2014, filed Oct. 29, 2014, and to Indian Patent Application No. 499/DEL/2014, filed Feb. 21, 2014, the disclosures of which are incorporated herein by reference in their entireties.

FIELD

This invention relates to (among other things) the field of cancer chemotherapy and involves the treatment of an individual suffering from a cancer by administering to the patient a long acting IL-2Rαβ-selective agonist in combination with another pharmacologically active agent.

BACKGROUND

The interleukin-2 receptor (IL-2R) is a heterotrimeric protein expressed on the surface of certain immune cells, such as lymphocytes, that binds and responds to the IL-2 cytokine. The IL-2 receptor is made up of 3 subunits—IL-2Rα, IL-2Rβ, and IL-2Rγ, with each of IL-2Rα and IL-2Rβ having binding affinity for IL-2 while IL-2Rγ alone has no appreciable affinity. Thèze et al. (1994) *Immunol. Today* 17(10):481-486. Further, the IL-2Rαβ heterodimer has a faster association rate and a slower dissociation rate when binding IL-2 versus either chain alone. Liparoto et al. *J. Mol. Recognit.* 12(5):316-321.

CD4+ regulatory T-cells, which are responsible for suppressing the immune response, preferentially express the IL-2Rαβ form of the IL-2R. Thus, administration of compounds that are agonists for IL-2Rαβ can be expected to suppress the immune response.

CD8+ memory T-cells, which are responsible for enhancing the immune response, preferentially express the IL-2Rβ form of the IL-2R. Thus, administration of compounds that are agonists for IL-2Rβ can be expected to enhance the immune response (by, e.g., increasing the proliferation of CD8+ memory T-cells).

Thus, administration of IL-2Rβ-selective agonists would be beneficial to patients suffering from certain cancers as doing so is expected to reduce the immune-suppressing effects of regulatory T-cells while increasing CD8+ memory T-cells, thereby recruiting the patient's own immune system to eliminate cancer cells. Optimally, such an IL-2Rβ-selective agonist would also exhibit relatively long exposure following administration, thereby further improving the patient's response to the treatment.

Recruiting the immune system of the cancer patient in the treatment of cancer via administration of IL-2β-selective agonists—which is directly immunoactivating—can be further enhanced through the administration of antagonists of immunosuppressive pathways (e.g., antagonists of CTLA-4 and PD-1).

Thus, the present invention seeks to address (among other things) the continuing need to provide more effective treatments of cancers by, for example, administering to a patient suffering from cancer an IL-2Bβ-selective agonist in combination with a pharmacological-based antagonist of a immunosuppressive pathway.

This and other needs in the art are addressed by the present invention.

SUMMARY

In one or more embodiments of the invention, a method is provided, the method comprising the steps of administering to a cancer patient: (a) an IL-2Rβ-activating amount of a long acting, IL-2Rβ-selective agonist; and (b) a CTLA-4 pathway-inhibiting amount of an anti-CTLA-4 antibody or a PD-1 pathway-inhibiting amount of an anti-PD-1 antibody. By way of clarity, with regard to the sequence of steps in accordance with this method, unless otherwise indicated, the method is not limited to the sequence of steps and step (a) can be performed before, after or simultaneously with, performing step (b).

Additional embodiments of the invention are set forth in the following description and claims.

BRIEF DESCRIPTION OF THE DRAWINGS

FIGS. 1, 2 and 3 are plots of mean tumor volumes, relative tumor volumes and body weights, respectively, associated with an efficacy study of a receptor-selective, long acting IL-2 agonist in combination with an anti-CTLA-4 antibody on a CT26 tumor model, which study is further described in Example 2.

FIGS. 4, 5 and 6 are plots of mean tumor volumes for 30 days, mean tumor volumes for 106 days, and body weights, respectively, associated with an efficacy study of a receptor-selective, long acting IL-2 agonist in combination with an anti-CTLA-4 antibody on an EMT6 tumor model, which study is further described in Example 3.

FIGS. 7 and 8 are plots of tumor volumes and body weights, respectively, associated with an efficacy study of a receptor-selective, long acting IL-2 agonist in combination with an anti-CTLA-4 antibody compared to that of Proleukin with an anti-CTLA-4 antibody on an EMT6 tumor model, which study is further described in Example 4.

FIGS. 9 and 10 are plots of tumor volumes and body weights, respectively, for 11 days associated with an efficacy study involving flow cytometry analysis of a receptor-selective, long acting IL-2 agonist in combination with an anti-CTLA-4 antibody on an EMT6 tumor model, which study is further described in Example 5.

FIGS. 11 and 12 each include graphs of tumor and spleen, respectively, of immune cell populations corresponding to the flow cytometry analysis further, described in Example 5.

FIGS. 13 and 14 are plots of mean tumor volumes and body weights, respectively, associated with an efficacy study of a receptor-selective, long acting IL-2 agonist in combination with an anti-PD-1 antibody on a CT26 tumor model, which study is further described in Example 6.

FIG. 15 shows two plots of mean tumor volumes and body weights following Phase I of a three phase re-challenge study further described in Example 7.

FIG. 16 shows two plots of relative mean tumor volumes and body weight changes following Phase I of a three phase re-challenge study further described in Example 7.

FIG. 17 shows a plot of relative body weight changes following Phase II of a three phase re-challenge study further described in Example 7.

FIG. 18 shows two plots of mean tumor volumes and body weights following Phase II of a three phase re-challenge study further described in Example 7.

FIG. 19 shows a plot of mean tumor volumes following Phase III of a three phase re-challenge study further described in Example 7.

FIG. 20 shows two plots of body weight changes and relative body weight changes Phase III of a three phase re-challenge study further described in Example 7.

FIG. 21 shows two plots of mean tumor volumes and individual tumor volumes over the course of a three phrase re-challenge study further described in Example 7.

FIG. 22 shows two plots of mean tumor volumes and body weights from day 0 to day 11 in connection with a RSLAIL-2 and anti-CTLA-4 combination study further described in Example 8.

FIG. 23 shows two plots of relative mean tumor volumes and body weights from day 0 to day 11 in connection with a RSLAIL-2 and anti-CTLA-4 combination study further described in Example 8.

FIG. 24 shows two plots of mean tumor volumes and body weights from day 0 to day 11 in connection with a RSLAIL-2 and anti-PD-1 combination study further described in Example 8.

FIG. 25 shows two plots of relative mean tumor volumes and body weights from day 0 to clay 11 in connection with a RSLAIL-2 and anti-PD-1 combination study further described in Example 8.

DETAILED DESCRIPTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic polymer" refers to a polymer that is at least 35% (by weight) soluble, preferably greater than 70% (by weight), and more preferably greater than 95% (by weight) soluble, in water at room temperature. Typically, an unfiltered aqueous preparation of a "water-soluble" polymer transmits at least 75%, more preferably at least 95%, of the amount of light transmitted by the same solution after filtering. It is most preferred, however, that the water-soluble polymer is at least 95% (by weight) soluble in water or completely soluble in water. With respect to being "non-peptidic," a polymer is non-peptidic when it has less than 35% (by weight) of amino acid residues.

The terms "monomer;" "monomeric subunit" and "monomeric unit" are used interchangeably herein and refer to one of the basic structural units of a polymer. In the case of a homo-polymer, a single repeating structural unit forms the polymer. In the case of a co-polymer, two or more structural units are repeated—either in a pattern or randomly—to form the polymer. Preferred polymers used in connection with the present invention are homo-polymers. The water-soluble, non-peptidic polymer comprises one or more monomers serially attached to form a chain of monomers.

"PEG" or "polyethylene glycol," as used herein, is meant to encompass any water-soluble poly(ethylene oxide). Unless otherwise indicated, a "PEG polymer" or a polyethylene glycol is one in which substantially all (preferably all) monomeric subunits are ethylene oxide subunits, though, the polymer may contain distinct end capping moieties or functional groups, e.g., for conjugation. PEG polymers for use in the present invention will comprise one of the two following structures: "—$(CH_2CH_2O)_n$—" or "—$(CH_2CH_2O)_{n-1}CH_2C_2$—," depending upon whether or not the terminal oxygen(s) has been displaced, e.g., during a synthetic transformation. As stated above, for the PEG polymers, the variable (n) ranges from about 3 to 4000, and the terminal groups and architecture of the overall PEG can vary.

"Branched,", in reference to the geometry or overall structure of a polymer, refers to a polymer having two or more polymer "arms" extending from a branch point.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two atoms within a given molecule but also on the substituents attached to these atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially", or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Pharmaceutically acceptable excipient" or "pharmaceutically acceptable carrier" refers to a component that may be included in the compositions of the invention causes no significant adverse toxicological effects to a patient.

The term "patient," refers to a living organism suffering from or prone to a condition that can be prevented or treated by administration of a compound of the invention as described herein, and includes both humans and animals.

As indicated above, the present invention is directed to (among other things) a method of administering to a patient suffering from a cancer, the method comprising the steps of: (a) an IL-2Rβ-activating amount of a long acting, IL-2β-selective agonist; and (b) a CTLA-4 pathway-inhibiting amount of an anti-CTLA-4 antibody or a PD-1 pathway-inhibiting amount of an anti-PD-1 antibody. With respect to administering steps (a) and (b), these administering steps can be performed in either order (as well as simultaneously) and the invention is not limited in this regard. In one or more embodiments of the invention, administering step (a) will be carried out before administering step (b). In one or more embodiments of the invention, administering step (b) will be carried out before administering step (a). In one or more embodiments, both administering steps (a) and (b) will be carried out simultaneously. Further, in one or more embodiments, steps (a) and/or (b) will be administered repeatedly. In addition, in or more embodiments, steps (a) and (b) will be carried out only once.

The treatment method described herein can continue for as long as the clinician overseeing the patient's care deems the treatment method is effective. Non-limiting parameters that indicate the treatment method is effective include the following: tumor shrinkage (in terms of weight and/or volume); a decrease in the number of individual tumor colonies; tumor elimination; and progression-free survival.

Exemplary lengths of time associated with the course of therapy in accordance with the claimed method include: about one week; two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about literature to obtain an appropriate frequency of administration (keeping in mind that some adjustment may be necessary in view of the combined effects of the treatment regimen).

The method described herein involves the administration of long acting, IL-2Rβ-selective agonist. In this regard, the invention is not limited to any specific long acting, IL-2Rβ-selective agonist so long as the agonist exhibits an in vitro binding affinity for IL-2Rβ that is at least 5 times greater (more preferably at least 10 times greater) than the binding affinity for IL-2Rαβ in the same in vitro model, and has at least an effective 10-fold in vivo half-life greater than IL-2 (half-life based on the in-vivo disappearance IL-2). By way of example, it is possible to measure binding affinities against IL-2 as a standard. In this regard, the RSLAIL-2 referenced in Example 1 of the present disclosure exhibits about a 60-fold decrease in affinity to IL-2Rαβ relative to IL-2, but only about a 5-fold decrease in affinity IL-2Rβ relative to IL-2.

Non-limiting examples of long acting, IL-2Rβ-selective agonists are described in WO 2012/065086. An exemplary long acting, IL-2Rβ-selective agonist is RSLAIL-2 referenced in Example 1 in the present application. In this regard, RSLAIL-2 is a composition comprising compounds encompassed by the following formula:

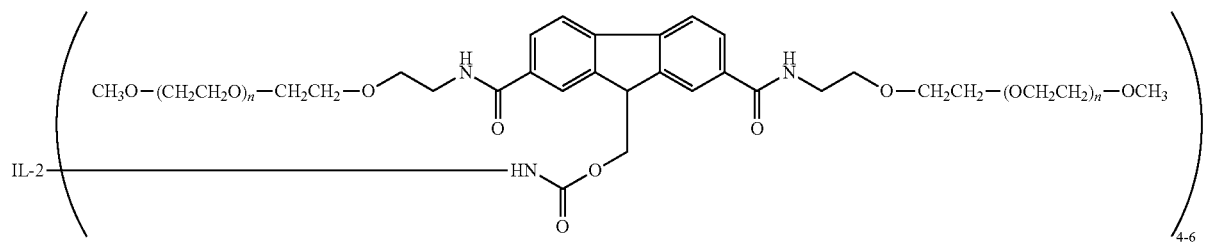

twenty-three months; about twenty-four months; about thirty months; about three years; about four years and about five years.

With regard to the frequency of administering the long acting, IL-2Rβ-agonist, one of ordinary skill in the art will be able to determine an appropriate frequency. For example, wherein IL-2 is a residue of IL-2, and pharmaceutically acceptable salts thereof. In one or more embodiments, the composition contains no more than 10% (based on a molar amount), preferably no more than 5% (based on a molar amount), of compounds encompassed by the following formula

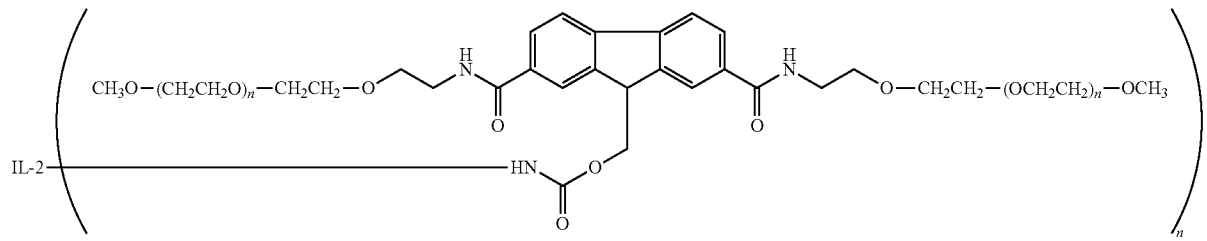

a clinician can decide to administer the long acting, IL-2β-selective agonist relatively infrequently (e.g., once every two weeks) and progressively shorten the period between dosings as tolerated by the patient. With regard to frequency of administering the anti-CTLA-4 antibody and anti-PD-1 antibody, the frequency for these agents can be determined in a similar fashion. In addition, as some long acting, IL-2Rβ-selective agonists, anti-CTLA-4 antibodies, anti-PD-1 antibody are either in advanced clinical testing or commercially available, it is also possible to refer to the wherein IL-2 is a residue of IL-2, (n) is an integer selected from the group consisting of 1, 2, 7 and >7, and pharmaceutically acceptable salts thereof.

The method described herein involves the administration of an anti-CTLA-4 antibody or an anti-PD-1 antibody. With regard to anti-CTLA-4 antibodies, these are known and include tremelimumab and ipilimumab. With regard to anti-PD-1 antibodies, these are known and include nivolumab and lambrolizumab, AMP-224, MDPL3280A, MEDI4736 and MSB0010718C.

Assays for determining whether a given compound can act as an anti-CTLA-4 antibody or anti-PD-1 antibody can be determined through routing experimentation by one of ordinary skill in the art.

In accordance with the method described herein, the long acting, IL-2Rβ-selective agonist is administered to a patient in an IL-2Rβ-activating amount. One of ordinary skill in the art can determine how much a given long acting, IL-2Rβ-selective agonist sufficient to provide clinically relevant agonistic activity at IL-2Rβ. For example, one of ordinary skill in the art can refer to the literature and/or administer a series of increasing amounts the long acting, IL-2Rβ-selective agonist and determine which amount or amounts provide clinically agonistic activity of IL-2β.

In one or more instances, however, the IL-2Rβ-activating amount is an amount encompassed by one or more of the following ranges: from about 0.01 to 1 mg/kg; from about 0.01 mg/kg to about 0.1 mg/kg; from about 1 mg/kg to about 1000 mg/kg; from about 2 mg/kg to about 900 mg/kg; from about 3 mg/kg to about 800 mg/kg; from about 4 mg/kg to about 700 mg/kg; from about 5 mg/kg to about 600 mg/kg; from about 6 mg/kg to about 550 mg/kg; from about 7 mg/kg to about 500 mg/kg; from about 8 mg/kg to about 450 mg/kg; from about 9 mg/kg to about 400 mg/kg; from about 5 mg/kg to about 200 mg/kg; from about 2 mg/kg to about 150 mg/kg; from about 5 mg/kg to about 100 mg/kg; from about 10 mg/kg to about 100 mg/kg; and from about 10 mg/kg to about 60 mg/kg.

In accordance with the method described herein, a CTLA-4 pathway-inhibiting amount of an anti-CTLA-4 antibody is administered or a PD-1 pathway-inhibiting amount of an anti-PD-1 antibody is administered. One of ordinary skill in the art can determine how much a given anti-CTLA-4 antibody or anti-PD-1 antibody is sufficient to provide clinically relevant inhibition of the CTLA-4 pathway or PD-1 pathway, respectively. For example, one of ordinary skill in the art can refer to the literature and/or administer a series of increasing amounts the anti-CTLA-4 antibody or anti-PD-1 antibody and determine which amount or amounts provide clinically relevant inhibition the CTLA-4 pathway or PD-1 pathway.

In one or more instances, however, the CTLA-4 and PD-1 pathway-inhibiting amounts are encompassed by one or more of the following ranges: from about 1 mg/kg to about 1000 mg/kg; from about 2 mg/kg to about 900 mg/kg; from about 3 mg/kg to about 800 mg/kg; from about 4 mg/kg to about 700 mg/kg; from about 5 mg/kg to about 600 mg/kg; from about 6 mg/kg to about 550 mg/kg; from about 7 mg/kg to about 500 mg/kg; from about 8 mg/kg to about 450 mg/kg; from about 9 mg/kg to about 400 mg/kg; from about 5 mg/kg to about 200 mg/kg; from about 2 mg/kg to about 150 mg/kg; from about 5 mg/kg to about 100 mg/kg; from about 10 mg/kg to about 100 mg/kg; and from about 10 mg/kg to about 60 mg/kg.

For confirmation, as used herein with regard to CTLA-4 and PD-1 pathway-inhibiting amounts of the of the anti-CTLA-4 antibody or anti-PD-1 antibody, respectively, the amount and extent of the inhibition can vary widely and the combination of either of these with the long acting, IL-2Rβ-selective agonist can still be effective. For example, an amount of the anti-CTLA-4 antibody or anti-PD-1 antibody that only minimally inhibits the CTLA-4 or PD-1 pathways, respectively, can still be an inhibiting amount as used herein so long as the method of the claimed invention results in a clinically meaningful response. So too, an amount of a long acting, IL-2Rβ-selective agonist that exhibits only minimal agonist activity IL-2Rβ for a sufficiently extended period of time can still be a long acting, IL-2Rβ-selective agonist so long as the method of the claimed invention results in a clinically meaningful response. In some instances, due to (for example) synergistic responses, minimal inhibition of the CTLA-4 or PD-1 pathways may only be required in the presence of the long acting, IL-2Rβ-selective agonist. In still other instances, due to (for example) synergistic responses, minimal agonist activity of IL-2Rβ may be required in the presence of CTLA-4 and PD-1 pathway inhibition.

The actual dose to be administered will vary depend upon the age, weight, and general condition of the subject as well as the severity of the condition being treated, the judgment of the health care professional, and conjugate being administered.

The invention provides a method for that is useful for (among other things) treating a patient suffering from a condition that is responsive to treatment with the compound. For example, patients may be responsive to the individual agents alone as well as the combination, but are more responsive to the combination. By way of further example, patients may be non-responsive to one of the individual agents, but are responsive to the combination. By way of still further example, patients may be non-responsive to either of the individual agents alone, but are responsive to the combination.

The method comprises administering a therapeutically effective amount of active agents via injection. Other modes of administration are also contemplated, such as pulmonary, nasal, buccal, rectal, sublingual and transdermal. As used herein, the term "parenteral" includes subcutaneous, intravenous, intra-arterial, intraperitoneal, intracardiac, intrathecal, and intramuscular injection, as well as infusion injections. Each pharmacological component of the method can be administered separately. Alternatively, if administration of two pharmacological components is desired to be simultaneous—and the two pharmacological components are compatible together and in a given formulation—then the simultaneous administration can be achieved via administration of single dosage form/formulation (e.g., intravenous administration of an intravenous formulation that contains both pharmacologically active agents). One of ordinary skill in the art can determine through routing testing whether two given pharmacological components are compatible together and in a given formulation.

The presently described method can be used to treat a patient suffering from any condition that can be remedied or prevented by this method. Exemplary conditions are cancers, such as, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma and leukemias.

All articles, books, patents, patent publications and other publications referenced herein are incorporated by reference in their entireties. In the event: of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

Anti-CTLA-4 antibody referenced in Examples 2-7 corresponds to anti-mouse CLTA-4 antibody purified from UC10-4F10-11 hybridoma cell line (ATCC). The cells were maintained in PFHM-II medium (Invitrogen) between the density of $1\times10^5$ and $1\times10^6$ cells/mL. Prior to purification, the medium was centrifuged to remove the cells. The pH of the medium was adjusted to 8 with NaOH, and its conductivity was lowered to 7 mS/cm by diluting with water. The pH/conductivity adjusted medium was loaded onto a Q-FF column, and the anti-mouse CLTA-4 antibody was eluted using a NaCl gradient.

The affinity of anti-CTLA-4 to its antigen was determined by Surface Plasmon Resonance (Biacore) and determined to be 20 pM.

Anti-PD-1 was purchased from BioXcell. It was obtained as a solution with the following characteristics: concentration: 4.76 mg/mL; endotoxin: <0.63 EU/mg; formulation: PBS pH 7; purity: >95%; isotype: rat IgG2a; and extinction coeff: 1.33. The affinity of anti-PD-1 to its antigen was measured by Surface Plasmon Resonance (Biacore) and found to be 1 nM. The purchased antibody was checked for purity by SDS-PAGE and SEC-HPLC and determined to be sufficiently pure for efficacy studies without further workup.

Example 1

PEGylation of rIL-2 with mPEG2-C2-fmoc-20K-NHS

PEGylation of rIL-2 with mPEG2-C2-fmoc-20K-NHS was previously reported in Example 2 of WO 2012/065085. There, the synthesis was reported to result in a mixture of 4-mers, 3-mers, 2-mers and 1-mers. Further analysis of the reaction, however, revealed higher degrees of attachment (e.g., 5-mers, 6-mers and 7-mers) were also produced. The present synthesis represents a scaled up approach for PEGylating IL-2 with mPEG2-C2-fmoc-20K-NHS.

Purified rIL-2 (106.4 mL) at 1.44 mg/ml was charged into a first vessel followed by the addition of 53.6 mL of formulation buffer (10 mM sodium acetate, pH 4.5, 5% trehalose). The pH was measured at 4.62 the temperature was measured at 21.2° C. The PEG reagent, C2-PEG2-FMOC—NHS-20K (available as described in WO 2006/138572) (13.1 g), was charged into a second vessel followed by the addition of 73.3 mL of 2 mM HCl. The resulting solution was swirled by hand for 25 minutes. Sodium borate (0.5 M, pH 9.8) was added to the first vessel to raise the pH to about 9.1 and then the second vessel containing the PEG reagent was added to the first vessel over one to two minutes. A rinse step was then performed by charging 8.1 mL of 2 mM HCl into the second vessel and added to the first vessel. In the conjugation reaction, the final rIL-2 concentration was 0.6 mg/mL, the sodium borate concentration was 120 mM, the pH was 9.1+/−0.2, the temperature was 20-22° C., and the molar ratio of PEG reagent to rIL-2, after adjustment for activity of the reagent (substitution level) is 35:1. The conjugation reaction was allowed to proceed for thirty minutes and then was stopped with an acidification reaction using 75 mL of 2N acetic acid (where pH drops to 4.01). The product of the reaction was diluted with water and the diluted PEGylated rIL-2 solution was filtered using a 0.2 micron filter and the filtered product is placed in sterile containers.

Thereafter, the diluted PEGylated rIL-2 solution was purified by loading the solution onto a chromatography column packed with SP sepharose FF resin (GE Healthcare). Following a washing step, the PEGylated rIL-2 are eluted using a sodium chloride gradient. Fractions containing 1-mers, 2-mers or 3-mers are eliminated while fractions containing 4-mers, 5-mers, 6-mers, 7-mers and any higher degrees of PEGylation are pooled, thereby resulting in a composition having primarily 4-mers, 5-mers and 6-mers (wherein 8-mers and higher degrees of PEGylation were found to be removed during a washing step associated with chromatography). This composition is the one used in connection with Examples 2-6 and referenced therein as "RSLAIL-2."

Yields of 4-mers, 5-mers and 6-mers were found to be increased (with a concomitant decrease in 1-mers, 2-mers and 3-mers) using the approach described in this example.

Example 2

Evaluating the Efficacy of RSLAIL-2 in Combination with Anti-CTLA-4 Antibody on the CT26 Tumor Model in Female BALB/c Mice The objective of this study was to evaluate the antitumor activity of RSLAIL-2 in combination with Anti-CTLA-4 antibody in the CT26 murine colon carcinoma tumor model in female BALB/c mice.

There were 5 groups with 12 animals in each group. Included were a vehicle control group treated on days 0, 4, 9 and 14, two single agent groups (Anti-CTLA-4 antibody treated on days 0, 4, 9, 14 and 18 or RSLAIL-2 on day 0 and 9) and two combined immunotherapy groups (Anti-CTLA-4 antibody plus RSLAIL-2) where Anti-CTLA-4 antibody (given on days 0, 4, 9, 14 and 18) treatment for one group was initiated at the same time as RSLAIL-2 (given on day 0, 4 and 9) and for the other, four days prior to RSLAIL-2 treatment initiation (given on days 4, 13 and 22). Treatment initiation for the study was performed 7 days after inoculation of CT26 cells at $2\times10^6$ cells/site at 0.1 mL injection volume. The tumor cells were injected subcutaneously in the abdominal area. The animals were distributed accordingly based on the randomization generated by the StudyLoge software. The mean tumor volumes on treatment day (Day 0) ranged from 111±9 $mm^3$ to 115±10 $mm^3$ (Mean±SEM).

Tumor volumes (in mm³) and body weights (in grams) were monitored 2 to 3 times a week and are presented in FIGS. 1 and 2, respectively, with details on the treatment schedule. The corresponding relative tumor values, standardized values calculated against individual tumor volumes at the start of the study and presented as percent growth are summarized in FIG. 1 (Day 0 to Day 30). Tumor free animals were monitored for tumor regrowth for 106 days and body weights were taken from treatment initiation.

Comparison of tumor volumes between vehicle control animals and treated animals on day 11 (last day the vehicle control animals were present) by One-way ANOVA with Tukey's post-test (GraphPad Prism version 6.03 for Windows, GraphPad Software, San Diego Calif.) showed all the treatment groups were significantly different from the vehicle control group.

Mean tumor growth inhibition (% TGI) was assessed on Day 11 (last day control animals were present) by using the following formula:

$$\% \text{ TGI} = (1 - (\text{Relative Tumor Volume (\%)}^{Treatment\ Group} \div \text{Relative Tumor Volume (\%)}^{Control\ Group}) \times 100$$

There was a 53% mean inhibition for Anti-CTLA-4 antibody (Gr. 2) treated tumors and 58% for the RSLAIL-2 group (Gr. 3). Combined immune therapy co-administration (RSLAIL-2 and Anti-CTLA-4 antibody initiated at the same time on Day 0) yielded 74% inhibition. Combined immune therapy with Anti-CTLA-4 antibody initiated on Day 0 and RSLAIL-2 treatment initiated on Day 4 (Gr. 5) yielded the greatest inhibition among the treatments at 88%.

One of the twelve (1/12) animals in group 4 were tumor free by day 14. A total of 4 animals were tumor free by day 28. In group 5, two (2/12) animals were tumor free by day 14 and a total of 8 animals were tumor free by day 25. See Table 1. All these animals from group 4 and 5 remained tumor free until study termination. (106 days from treatment initiation).

Mean body weights ranged from 17.4±0.3 g to 18.2±0.3 g (Mean±SEM) on treatment day. No significant mean body weight loss below baseline during the treatment phase was observed from any of the treatment groups (FIG. 3).

Example 3

Evaluating the Efficacy of RSLAIL-2 in Combination with Anti-CTlA-4 Antibody on the EMT6 Tumor Model in Female BALB/c Mice The objective of this study was to evaluate the antitumor activity of RSLAIL-2 in combination with Anti-CTLA-4 antibody on the EMT6 murine mammary carcinoma tumor model in female BALB/c mice.

There were 5 groups with 12 animals each in each group. Included were a vehicle control group treated on days 0, 4, 9 and 14, two single agent groups (Anti-CTLA-4 antibody treated on days 0, 4, 9, 14 and 18 or RSLAIL-2 on day 0 and 9) and two combined immunotherapy groups (Anti-CTLA-4 antibody plus RSLAIL-2) where Anti-CTLA-4 antibody (given on days 0, 4, 9, 14 and 18) treatment for one group was initiated at the same time as RSLAIL-2 (given on day 0, 4 and 9) and for the other, four days prior to RSLAIL-2 treatment initiation (given on days 4, 13 and 22). Treatment initiation for the study was performed 7 days after inoculation of EMT6 cells at 2×10⁶ cells/site at 0.1 mL injection volume. The tumor cells were injected subcutaneously in the abdominal area. The animals were distributed accordingly based on the randomization generated by the StudyLog® software. The mean tumor volumes on treatment day (Day 0) ranged from 144±8 mm³ to 147±10 mm³ (Mean±SEM).

Tumor volumes (in mm³) and body weights (in grams) were monitored 2 to 3 times a week and tumor volume data are presented in FIG. 4 (Day 0 to Day 30) with details on the treatment schedule. Tumor-free animals were monitored for tumor regrowth for 106 days, from treatment initiation which is presented in FIG. 5.

Comparison of tumor volumes between vehicle control animals and treated animals on day 18 (last day the vehicle control animals were present) by One-way ANOVA with Tukey's post-test (GraphPad Prism version 6.03 for Win-

TABLE 1

| | | | Tumor Volumes (Mean ± SEM in mm³) | | | | |
|---|---|---|---|---|---|---|---|
| Treatment | Dose | N | Tumor Volume on Treatment Initiation (Day 0) (MEAN ± SEM) | Tumor Volume on Day 11 (MEAN ± SEM) | Mean Tumor Growth Inhibition (%) (Endpoint: 18 Days) | Mean Tumor Delay (Days) | Tumor Free Animals on Termination |
| 1. Vehicle Control | NA | 12 | 111 ± 9 | 1499 ± 196 | NA | | 1[1] of 12 (Day 18) |
| 2. Anti CTLA-4 Antibody | 100 ug | 12 | 115 ± 10 | 732 ± 165 | 53.3 | | 1[1] of 12 (Day 18) |
| 3. RSLAIL-2 | 0.8 mg/kg | 12 | 111 ± 11 | 600 ± 143 | 58.4 | | 1[1] of 12 (Day 18) |
| 4. RSLAIL-2 (Day 0) + ANTI-CTLA-4 ANTIBODY (Day 0) | 100 ug 0.8 mg/kg | 12 | 113 ± 12 | 414 ± 115 | 74.2 | | 4 of 12 (Day 106) |
| 5. RSLAIL-2 (Day 4) + ANTI-CTLA-4 ANTIBODY (Day 0) | 0.8 mg/kg 100 ug | 12 | 111 ± 9 | 170 ± 27 | 88.1 | | 8 of 12 (Day 106) |

[1]The group (including this animal) was collectively removed from the study on Day 18 dows, GraphPad Software, San Diego Calif.) showed a significant difference between the vehicle controls (group 1) versus group 2 (Anti-CTLA-4 antibody treatment) and group 5 (Anti-CTLA-4 antibody started on Day 0+RSLAIL-2 started on Day 4). No statistical difference was noted between group 1 (vehicle controls) versus group 3 (RSLAIL-2 alone) and group 4 (RSLAIL-2+Anti-CTLA-4 antibody both treatments initiated on day 0).

Mean tumor growth inhibition (% TGI) was assessed on Day 18 (last day control animals were present) by using the following formula:

% TGI=(1−(Relative Tumor Volume (%)$^{Treatment\ Group}$÷Relative Tumor Volume (%)$^{Control\ Group}$)×100

There was a 55% mean inhibition for Anti-CTLA-4 antibody (Gr. 2) treated tumors and 22% for the RSLAIL-2 group (Gr. 3). Combined immune therapy co-administration (RSLAIL-2 and Anti-CTLA-4 antibody initiated at the same time on Day 0) yielded 27% inhibition. Combined immune therapy with Anti-CTLA-4 antibody initiated on Day 0 and RSLAIL-2 treatment initiated on Day 4 (Gr. 5) yielded the greatest inhibition among the treatments at 92%. The tumor on one animal in the vehicle control group was observed to have completely autoregressed by day 11. In spite of this, mean tumor volume was 1789 mm$^3$±196 (MEAN±SE, N=12) by Day 18 when the group was collectively removed from the study. One of the twelve animals in group 4 was also tumor free by day 18. Mean tumor volume for the rest of the group was 1361±214 mm$^3$ when the whole group was removed from the study (on Day 18).

Five of the twelve (5/12) animals in group 5 were tumor free by day 14. A total of 10 animals were tumor free by day 18. All 10 animals remained tumor free until termination of the study (106 days from treatment initiation). See Table 2.

Mean body weights ranged from 17.8±0.3 g to 18.4±0.4 g (Mean±SEM) on treatment day (FIG. 6). No significant body weight loss was observed from any of the treatment groups.

Example 4

Evaluating the Efficacy of RSLAIL-2 in Combination with Anti-CTLA-4 Antibody Compared to that of Proleukin with Anti-CTLA-4 Antibody Treatment on the EMT6 Tumor Model in Female BALB/c Mice The objective of this study is to evaluate the antitumor activity of RSLAIL-2 in combination with Anti-CTLA-4 antibody and compare it to that of Proleukin on the EMT6 murine mammary carcinoma tumor model in female BALB/c mice.

There were 7 groups with 10 animals each. Included were an Antibody Control (Gr. 1) given on days 0, 4, 8 and 13) and three single agent groups. These were Anti-CTLA-4 antibody (Gr. 2) given on days 0, 4, 8, 13 and 18. Proleukin (Gr. 3) given from day 0 to 4 then 7 to 11 and a RSLAIL-2 (Gr. 4) given on day 0 and 9. Also included were three combined immune therapy groups. A combined immunotherapy group using Anti-CTLA-4 antibody with Proleukin (Gr. 5) and 2 combination treatment group using Anti-CTLA-4 antibody with RSLAIL-2 (Gr. 6 and 7) on different treatment schedules. Anti-CTLA-4 antibody regimen was initiated on day 4 and given again on days 9 and 13 while RSLAIL-2 was initiated on day 0 and given again on day 9 for group 6. Anti-CTLA-4 antibody therapy for group 7 was initiated on day 0 and given again on days 4, 8 and 13 while RSLAIL-2 was initiated on day 4 and given again on days 13 and 22. Treatment initiation (Day0) was designated as 7 days after inoculation of EMT6 cells at 2×10$^6$ cells/site at 0.1 mL injection volume on the mice. The tumor cells were injected subcutaneous in the abdominal area. The animals were distributed accordingly on Day 0 based on the randomization generated by the StudyLog® software. The mean tumor volumes on treatment day ranged from 159±7 mm$^3$ to 170±8 mm$^3$ (Mean±SE).

TABLE 2

Tumor Volumes (Mean ± SE in mm$^3$)

| Treatment | Dose | N | Tumor Volume on Treatment Initiation (Day 0) (MEAN ± SEM) | Tumor Volume on Day 18 (MEAN ± SEM) | Mean Tumor Growth Inhibition (%) (Endpoint: 18 Days) | Tumor Free Animals on Termination |
|---|---|---|---|---|---|---|
| 6. Vehicle Control | NA | 12 | 147 ± 10 | 1789 ± 196 | NA | 1[1] of 12 (Day 18) |
| 7. Anti CTLA-4 | 100 ug | 12 | 145 ± 9 | 824 ± 185 | 55 | None |
| 8. RSLAIL-2 | 0.8 mg/kg | 12 | 144 ± 11 | 1405 ± 13 | 22 | None |
| 9. RSLAIL-2 (Day 0) + ANTI-CTLA-4 ANTIBODY (Day 0) | 100 ug 0.8 mg/kg | 12 | 145 ± 10 | 1361 ± 214 | 27 | 1[1] of 12 (Day 18) |
| 10. RSLAIL-2 (Day 4) + ANTI-CTLA-4 ANTIBODY (Day 0) | 0.8 mg/kg 100 ug | 12 | 144 ± 8 | 155 ± 83 | 92 | 10 of 12 (Day 107) |

[1]The group (including this animal) was collectively removed from the study on Day 18

Tumor volumes (in mm³) and body weights (in grams) were monitored 2-3 times a week and are presented in the FIGS. 7 and 8, respectively (Day 0 to Day 28). Tumor Free animals were monitored regrowth and health conditions for 99 days (from treatment initiation).

Comparison of tumor volumes between control animals and treated animals on day 18 (last day the vehicle control animals were present) by One-way ANOVA with Tukey's post-test (GraphPad Prism version 6.03 for Windows, GraphPad Software, San Diego Calif.) showed that only group 5 (Anti-CTLA-4 antibody+Proleukin) and group 7 (Anti-CTLA-4 antibody+ RSLAIL-2) were significantly different from those of controls. However, although significantly different from controls, mean tumor volume of the two treatment groups were not significantly different from one another.

Mean tumor growth inhibition (% TGI) was assessed on Day 18 (last day control animals were present) by using the following formula:

$$\% \text{ TGI} = (1 - (\text{Relative Tumor Volume } (\%)^{Treatment\ Group} \div \text{Relative Tumor Volume } (\%)^{Control\ Group}) \times 100$$

There was a 27% mean inhibition for Anti-CTLA-4 antibody treatment alone (Gr. 2). Inhibition of tumor growth was 24% by Proleukin (Gr. 3) and 5% by RSLAIL-2 (Gr. 4), combined immune therapy with Anti-CTLA-4 antibody and Proleukin (GR 5) yielded 26% inhibition, RSLAIL-2 with Anti-CTLA-4 antibody treatment (Gr. 6) gave a 2% inhibition while group 7 (Anti-CTLA-4 antibody with RSLAIL-2) yielded a 94% inhibition.

Several animals were observed to be tumor free by day 18. There were three (3/10) from group 5, one (1/10) from group 6 and five (5/10) in group 7. By study termination (Day 99), the total number of tumor free animals were from groups 5, 6 and 7 were 4/10, 1/10 and 7/10 respectively. See Table 3.

Example 5

Efficacy Study Testing RSLAIL-2 in Combination with Anti-CTLA-4 Antibody on the EMT6 Tumor Model in Female BALB/c Mice (Day 0, 3 and 11 Sample Collection for Flow Cytometry Analysis)

Prior combination RSLAIL-2 and Anti-CTLA-4 antibody efficacy studies suggest synergy in the EMT6 mouse mammary model. The objective of this study was to evaluate/assess the antitumor activity of RSLAIL-2 in combination with Anti-CTLA-4 antibody on the EMT6 murine mammary carcinoma tumor model in female BALB/c mice. In addition, in order to identify immune population responsible for combinatorial efficacy, tissue (tumor and spleen) was collected and processed at 0, 3 and 11 days after treatment initiation. Identification and quantification of immune cells that infiltrated the tissues was evaluated by flow cytometry analysis. The results were compared between treatment groups.

In-Vivo Phase

There were 6 treatment groups in this study with 3-10 animals in each group. Included was an Antibody control, IgG2a (Group 1), given at 100 ug/mouse on day 0, 4, and 8; an Anti-CTLA-4 antibody treatment (Group 2), given at 100 ug/mouse on day 4 and 8; Proleukin treatment (Group 3), given at 0.5 mg/kg on days 4 to day 8; and RSLAIL-2 treatment (Group 5), given a single administration at 0.8 mg/kg on day 4. Also included were three groups to be treated with a combination of Anti-CTLA-4 antibody (100 ug/mouse given on day 0, 4, and 8) and Proleukin (0.5 mg/kg given on day 4 to day 8), Group 4 or RSLAIL-2 (0.8 mg/kg given on day 4), Group 6.

Treatment was initiated 7 days after the animals were inoculated with $2 \times 10^6$ cells/site of EMT6 murine mammary

TABLE 3

| Treatment Group | Dose | N | Tumor Volume on Treatment Initiation (Day 0) (MEAN ± SEM) | Tumor Volume on Day 18 (MEAN ± SEM) | Mean Tumor Growth Inhibition (%) (Endpoint: 18 Days) | Tumor Free Animals on Termination |
|---|---|---|---|---|---|---|
| 1. Antibody Control (Day 0, 4, 8, 13) | 100 ug | 10 | 166 ± 6 | 1803 ± 174 | NA | NA |
| 2. Anti CTLA-4 antibody (Day 0, 4, 8, 13) | 100 ug | 10 | 166 ± 7 | 1294 ± 122 | 27 | None |
| 3. Proleukin (Day 0-4, 7-11) | 0.5 mg/kg | 10 | 165 ± 7 | 1335 ± 236 | 24 | None |
| 4. RSLAIL-2 | 0.8 mg/kg | 10 | 167 ± 8 | 1040 ± 78 | 5 | None |
| 5. Anti-CTLA-4 antibody (Day 0) + Proleukin (Day 4) | 0.8 mg/kg 0.5 mg/kg | 10 | 159 ± 7 | 155 ± 83 | 76 | 4 of 10 (Day 99) |
| 6. RSLAIL-2 (Day 0) + Anti-CTLA-4 antibody (Day 4) | 0.8 mg/kg 100 ug | 10 | 165 ± 7 | 1701 ± 229 | 2 | 1 of 10 (Day 99) |
| 7. Anti-CTLA-4 antibody (Day 0) + RSLAIL-2 (Day 4) | 100 ug 0.8 mg/kg | 10 | 170 ± 8 | 108 ± 56 | 94 | 7 of 10 (Day 99) |

Tumor Volumes (Mean ± SE in mm³)

carcinoma cells (0.1 mL) subcutaneously, in the abdominal region. The mice were distributed into treatment groups according to tumor volumes.

The animals were sacrificed and tissue (tumor and spleen) were collected at Day 0 (Naïve Controls), Day 3 (Group 1 and 6), group 6 day 3 animals had been dosed with only Anti-CTLA-4 antibody at this time, addition of RSLAIL-2 begin at day 4, samples were also taken at Day 11 (all groups) after treatment initiation. Three animals were selected for each collection day. The animals selected had intact tumors (non-necrotic) and volumes that best approximated the group mean tumor volume for that day.

Mean tumor volume was 164±10 mm$^3$ for naïve group on treatment day 0. On day 3, mean tumor volumes were 282±7 mm$^3$ and 333±26 mm$^3$ (Mean±SEM), respectively for Group 1 and Group 6. On day 11, mean tumor volumes were 843±138 mm$^3$ for Group 1, 1059±135 mm$^3$ for Group 2, 814±70 mm$^3$ for Group 3, 832±262 mm$^3$ for Group 4, 620±103 mm$^3$ for Group 5, and 255±11 mm$^3$ for Group 6 (Mean±SEM). See FIG. 9.

Animals were weighed at least once a week. The mean body weights were 18.9±0.3, 18.6±0.3, 19.2±0.2, 18.7±0.2 17.8±0.3, 18.9±0.3 grams for Groups 1, 2, 3, 4, 5, and 6, respectively, on treatment day (Day 0). On Day 3, the mean body weights for Group 1 and 6 were 19.1±0.7 and 19±0.3 grams respectively. Mean body weights on Day 11 were 19.8±0.2, 19.4±0.2, 19.9±0.2, 20±0.5, 19.6±0.4 and 19.5±0.4 grams (Mean±SEM) for groups 1, 2, 3, 4, 5, and 6 respectively. See FIG. 10.

Ex-Vivo Phase

Collected tissue samples were manually minced using a scalpel followed by a 13 minute enzymatic digestion incubated at 37° C. The components of the digestion buffer were of 2.5 mg/ml Collagenase Type II (GIBCO BRL), 2.5 mg/ml Collagenase Type IV (GIBCO BRL), and 0.5 mg/ml DNase (Sigma-Aldrich) in PBS/BSA. After incubation, the digest was quenched by adding Waymouth's MB (GIBCO BRL) containing 10% FBS (heat inactivated; GIBCO BRL) and filtered through a 70-uM nylon filter (Falcon) that yielded a single cell suspension. The cells were washed in HBSS and centrifuged, then resuspended in fresh HBSS. An aliquot was taken from each sample for counting then stained with eFlour-450 viability dye. The samples were then plated in a 96-deep well plate, stained and collected for flow cytometry analysis.

The tumor and spleen cell samples were first treated with a fixable viability indicator and then stained for viable immune cells, CD3, CD4, CD8, CD25, CD44, CD122, Foxp3 (internal stain), DX5 and NKp46 surface antigens.

The total amount of live immune cells were counted for each of the samples (3 per treatment group) and used for gating/collecting total events for CD4+, TREG+ cell, CD8+, Memory effector CD8+ cells, total NK cells, mature NK cells (which were normalized to 1 cubic millimeter of tumor tissue) as well as the total cell counts for the spleen for each of the treatment groups. The primary counts were derived from the summarized raw data of the flow cytometer reading and analyzed using FlowJo.

Flow Cytometry

Three naïve animals were sacrificed on day 0. Three animals were sacrificed from Group 1 (having received isotype control) and from Group 6 (having received Anti-CTLA-4 antibody treatments only) on day 3, and three animals from all Groups 1-6 were sacrificed on day 11 after the initiation of treatment.

The graphical representation of the data can be found in FIG. 11 and FIG. 12 for Day 11 in tumor and spleen, respectively.

There is no difference in CD4+ or regulatory T cell population (from Day 3-Day 11) when treated with Anti-CTLA-4 antibody alone. Pre-treatment with Anti-CTLA-4 antibody followed by Proleukin or RSLAIL-2 treatment increases CD4+ population; however, there is no difference in regulatory T cell population (Anti-CTLA-4 antibody vs. Anti-CTLA-4 antibody+ RSLAIL-2 or Proleukin). There is no difference in CD4+ cells in RSLAIL-2+Anti-CTLA-4 antibody vs. RSLAIL-2 alone; however, RSLAIL-2+Anti-CTLA-4 antibody reduces regulatory T cell population when compared to RSLAIL-2. There is a large population of CD4+ cells in the RSLAIL-2+Anti-CTLA-4 antibody group that are not accounted for; these results suggest that the majority of these cells are not Tregs.

Pre-treatment with Anti-CTLA-4 antibody followed by RSLAIL-2 treatment significantly increases CD8+ population, P=0.0078, and memory effector CD8 cells, P=0.0058. (Two tailed t test Anti-CTLA-4 antibody+RSLAIL-2 vs. Anti-CTLA-4). In addition, RSLAIL-2+Anti-CTLA-4 antibody significantly increase CD8+ and memory effector CD8 cells when compared to RSLAIL-2 alone.

Anti-CTLA-4 antibody alone had no trending effect on total NK cell population; however, mature NK cells were significantly decreased (P=0.0278 from day 3 to day 11). Pretreatment with Anti-CTLA-4 antibody followed by RSLAIL-2 treatment increases total NK population and mature NK cell population. No difference in mature NK cells in RSLAIL-2+Anti-CTLA-4 antibody group when compared to RSLAIL-2 group.

Example 6

Efficacy of Combined Immune Therapy with RSLAIL-2 and Anti-PD-1 Antibody on CT26 Murine Colon Carcinoma Tumor Growths in Female BALB/c Mice The objective of this study was to evaluate the antitumor activity of combined immune therapy with RSLAIL-2 and Anti-PD-1 antibody on the CT26 murine colon carcinoma tumor model in female BALB/c mice.

There were 4 groups with 10 animals each. Included were a vehicle Control group (Gr. 1), an Anti-PD-1 antibody treatment group, an RSLAIL-2 treatment group (Gr. 3) and a combination treatment group treated first with Anti-PD-1 antibody (200 ug) on days and RSLAIL-2 (0.8 mg/kg) 4 days after. CT26 cells at 2×10$^6$ cells/site in 0.1 mL injection volume were implanted on the mice subcutaneously in the abdominal area. Treatment was initiated seven days after tumor cell inoculation (Day 0). The animals were distributed accordingly on Day 0 based on the randomization generated by the StudyLoge software. The mean tumor volumes on treatment day (Day 0) ranged from 123±5 mm$^3$ to 127±6 mm$^3$ (Mean±SE).

Tumor volumes (in mm$^3$) and body weights (in grams) were monitored 2 to 3 times a week and are presented in the FIGS. 13 and 14, respectively. The study was monitored for 16 days.

Comparison of tumor volumes between control animals and treated animals on day 12 (last day the vehicle control animals were present) by One-way ANOVA with Tukey's post-test (GraphPad Prism version 6.03 for Windows, GraphPad Software, San Diego Calif.) showed that tumor volumes for all the treatment groups were significantly different from those of untreated controls.

Percent Tumor Growth Inhibition (% TGI) was calculated using the following formula:

% TGI=(1−(Relative Tumor Volume (%)$^{Treatment\ Group}$+Relative Tumor Volume (%)$^{Control\ Group}$)×100

There was a 55% and a 58% mean tumor growth inhibition observed with Anti-PD-1 antibody (Gr. 2) and RSLAIL-2 (Gr. 3) respectively. Tumor growth inhibition for the group given both treatments in combination (Gr. 4) was observed at 83%. Five (5/10) animals in group 4 at study termination had tumors with volumes less than their initial volumes on Day 0.

Mean Tumor Volume Quadrupling Time (TVQT), time in days it takes tumors to grow to 4 times their initial volume was interpolated using non-linear second degree polynomial analysis (GraphPad Prism version 6.03 for Windows, GraphPad Software, San Diego Calif.) to assess Tumor Growth Delay (TGD). Mean tumor volume quadrupling time for control tumors was 5.2 days, 7.6 days for Group 3 (Anti-PD-1 antibody), 8.2 days for Group 3 (RSLAIL-2) and 15.6 for the combined immune therapy group (Gr. 4). Mean tumor growth delay for Group 2, Group 3 and Group 4 are 2.4 days, 3.0 days and 10.4 days, respectively. See Table 4.

Example 7

Re-Challenge Study

Re-Challening Tumor-Free Animals with EMT6 Murine Mammary Carcinoma Tumors after Effective Combined Immune Therapy with RSLAIL-2 and Anti-CTLA-4

The objective of this example was to evaluate the extent and duration of efficacy when treating mice implanted with EMT6 mammary carcinoma tumors with combined immune therapy using RSLAIL-2 and a commercially available rodent Anti-CTLA-4 checkpoint blockade antibody. As previously demonstrated in Examples 2-6, this combination yields significant tumor free animals and by re-challenging tumor-free animals with EMT6 tumor cells or CT26 tumor cells, the ability of this combination to elicit tumor-specific responses are evaluated.

This re-challenge study was conducted in three phases.

The initial part of the study ("Phase I") used 80 female BALB/c mice bearing EMT6 (Murine Mammary Carcinoma) tumors. Ten (10/80) animals were randomly selected and assigned to the antibody control group (100 µg on Days 0, 4, 9, 13 i.p.). The rest of the animals (70/80) were treated with a combination of Anti-CTLA-4 i.p. (100 µg on Days 0, 4, 9, 13 and 18) and RSLAIL-2 i.v. (0.8 mg/kg on Days 4, 13 and 22).

Treatment initiation (Day 0) was designated as seven days after inoculation of EMT6 cells at 2×10$^6$ cells/site in 0.1 mL injection volumes, injected subcutaneously in the abdominal

TABLE 4

Tumor Volumes (Mean ± SE in mm$^3$)

| Treatment | Dose | N | Tumor Volume on Treatment Initiation (Day 0) (MEAN ± SE) | Tumor Volume on Day 12 (MEAN ± SE) | Mean Tumor Growth Inhibition (%) (Endpoint: 12 Days) | Mean Group TVQT (Days) | Mean Group TGD (Days) |
|---|---|---|---|---|---|---|---|
| 1. Antibody Control (Day 0, 4, 8, 13) | 200 ug | 10 | 125 ± 5 | 1983 ± 248 | NA | 5.2 | NA |
| 2. Anti PD1 antibody (Day 0, 4, 8, 13) | 200 ug | 10 | 126 ± 5 | 897 ± 82 | 55 | 7.6 | 2.4 |
| 3. RSLAIL-2 (Day 0, 9) | 0.8 mg/kg | 10 | 127 ± 6 | 833 ± 176 | 58 | 8.2 | 3.0 |
| 4. Anti PD1 antibody (Day 0, 4, 8, 13) + RSLAIL-2 (Day 0, 9) | 200 ug 0.8 mg/kg | 10 | 123 ± 5 | 334 ± 109 | 83 | 15.6 | 10.4 |

Mean body weights ranged from 17.5±0.2 g to 18.1±0.2 g (Mean±SEM) on Day 0 (FIG. 13). No significant body weight loss was observed (FIG. 14) except for one animal in Group 2 which was removed from the study on day 12. Necropsy revealed a metastatic lesion in the pulmonary cavity.

Greater tumor growth inhibition (TGI) and tumor growth delay (TGD) was observed in the animals given a combination of Anti-PD-1 and RSLAIL-2 than those treated with either single agent.

area. The mean tumor volumes on treatment initiation were 206±15 and 222±8 (MEAN±SE) for the vehicle control and treatment group respectively.

Phase I was monitored until Day 48. Tumor volumes (in mm$^3$) and body weights (in grams) were measured 2 to 3 times a week and presented in FIG. 15. The corresponding relative tumor volumes, standardized values calculated against individual tumor volumes at the start of the study (Day 0) and presented as percent growth and the relative changes in body weight are summarized in FIG. 16.

The results from Phase I of the study showed a Tumor Growth Inhibition (TGI) of 73% (P<0.0001), calculated using mean relative tumor volumes between control animals (698%) and treated animals (189%) on day 14 (last day all the control animals were present) and then compared using unpaired t-test with Welches correction factor (GraphPad Prism version 6.03 for Windows, GraphPad Software, San Diego Calif.).

The Mean Tumor Growth Delay (TGD) of the animals (N=39) in Phase I that did not exhibit complete response to the combined immune therapy was 12.7 days (P<0.0001). Tumor Volume Quadrupling Time (TVQT) was computed by using interpolated individual tumor time to 400% growth with second order polynomial non-linear regression analysis (GraphPad Prism). Tumor-free animals (complete responders) were not included in the assessment for TGD.

In Phase I, treated animals were observed with rough coats (slight) around 5 days after the first and second RSLAIL-2 administration. Rough coats were not observed after the third administration. No significant body weight losses were observed (FIG. 16).

A summary of the results from Phase I of the study are provided in Table 5.

re-challenged with CT26) were bearing tumors with mean volumes of 167±22 and 177±11 respectively (MEAN±SE). Only 85% tumor uptake rate was observed in Group 3 (EMT6 Tumor Free Animals Re-challenged with EMT6) five days after inoculation. Tumor volumes were observed to be relatively smaller than those on in the other groups. Mean tumor volume was 62±8 mm$^3$. Fourteen of the twenty (70%) animals in this group were tumor free (completely rejected EMT6 tumor implants) 17 clays after re-challenge and remained tumor free until the end of Phase II (Day 109).

Animals in Group 2, EMT6 tumor free animals after combined immune-therapy in Phase I and re-challenged with CT26 tumors, had a mean tumor volume of 1257±201 (Mean±SE) 14 days after re-challenge and a mean time to grow to 1000 mm$^3$ volume of 13.6±0.8. Tumor growth did not appear to be affected by Phase I therapy which implies tumor-type specificity of the immune response. See the summary of the results from Phase II of the study provided in Table 7.

TABLE 5

Phase I Summary of Results (Mean ± SE)

| Treatment | Dose | N | Tumor Volume on Treatment Initiation (mm$^3$) | Mean Relative Tumor Volume on Day 14 (%) | Mean Tumor Growth Inhibition (%) On Day 14 | TVQT (Days) | Tumor Growth Delay (Days) | Tumor Free Animals by Day 48 |
|---|---|---|---|---|---|---|---|---|
| Antibody Control (Day 0, 4, 8, 13) | NA | 10 | 206 ± 15 | 698 ± 60 | NA | 9.7 | NA | NA |
| RSLAIL-2 (Day 4, 13, 22) + Anti CTLA-4 (Day 0, 4, 9, 13, 18) | 0.8 mg/kg 100 ug | 70 | 222 ± 8 | 189 ± 25 | 73 (P < 0.0001) | [1]22.4 | [1]12.7 (P < 0.0001) | 31 (44%) |

[1]Only interpolated for animals with partial response, animals with complete response (i.e. tumor free) were not included
[2]Mean tumor growth inhibition (% TGI) was assessed on Day 18 (last day control animals were present) by using the formula: % TGI = (1 − (Relative Tumor Volume (%)$^{Treatment\ Group}$ ÷ Relative Tumor Volume (%)$^{Control\ Group}$) × 100

The next part of the study, ("Phase II") was initiated on Day 49. A total of 40 animals (10 age-appropriate naïve animals and 30 animals that completely responded to the RSLAIL-2+Anti CTLA-4 combined immune-therapy) were used for 3 groups and distributed as described in Table 6.

TABLE 6

Phase II Study Design

| [1]Group | N |
|---|---|
| Age Appropriate Naïve Animals Challenged with EMT6 Cells | 10 |
| EMT6 Tumor-Free Animals Re-challenged with CT26 | 10 |
| EMT6 Tumor-Free Animals Re-challenged with EMT6 | 20 |

[1]Tumor Free Animals refer to EMT6 tumor bearing animals from Phase I that completely responded to the RSLAIL-2 + Anti CTLA-4 therapy On Day 49, the animals were implanted with either EMT6 or CT26 tumor cells (2×10$^6$ in 0.1 mL media), injected subcutaneously in the abdominal region.

The results from Phase II of the study showed tumor uptake and growth on the animals were evident five days after inoculation (Day54). All the animals in Group 1 (Age Appropriate Naïve) and Group 2 (EMT6 tumor-free animals One animal from Group 1 was found expired on day 14. Necropsy revealed what appeared to be metastatic lesions in the lungs (not verified by histology) and bloody fluid in the chest cavity. Other than this, no other clinical observations or significant body weight loss was noted. See FIG. 17.

Mean tumor volumes (FIG. 18) between the Age Appropriate Naïve animals (1541±144 mm$^3$) and the EMT6 tumor free animals re-challenged with EMT6 (192±107) were compared 21 days after implantation to assess TGI (87.5%).

TVQT could not be assessed due to a lack of baseline tumor volume starting point. In its place, time for tumor growth to 1000 mm$^3$ volume for each of the tumor-bearing animals were interpolated (using second order polynomial non-linear regression analysis of GraphPad Prism) to aid in assessing and approximate tumor growth delay. Time (in days) taken for growth to 1000 mm$^3$ tumor volume were 16.9±1 and 13.6±0.8 (Mean±SE) days for Groups 1 and 2, respectively. Only the animals (6/20) that did not completely reject EMT6 re-challenge in Group 3 were assessed for time to 1000 mm$^3$ growth, which was 30.3±5.5. Mean tumor growth to 1000 mm$^3$ delay for these animals was calculated to be 13.4 days.

TABLE 7

Phase II Summary of Results (Mean ± SE)

| Treatment | N | Mean Tumor Volume on Day 5 | Time taken to grow to 1000 mm³ (Days) | Tumor Growth Delay (Days to 1000 mm³) | Mean Tumor Volume 21 days after tumor implantation (mm³) | Mean Tumor Growth Inhibition (%) On Day 21 | Tumor-Free Animals by Day 109 |
|---|---|---|---|---|---|---|---|
| Age Appropriate Naïve Animals Challenged with EMT6 | 10 | 167 ± 22 | 16.9 ± 1 | NA | 1541 ± 144 | NA | NA |
| EMT6 Tumor-Free Animals Re-challenged with CT26 | 10 | 177 ± 11 | 13.6 ± 0.8 | NA | NA | NA | NA |
| EMT6 Tumor-Free Animals Re-challenged with EMT6 | 20 | 62 ± 8 | 30.3 ± 5.5 (6/20 animals) | 13.4 (6/20 Animals) | 192 ± 107 | 87.5 | 14 |

The final part of the study (Phase III) was designated over Days 109 to 168. Animals (N=14) that completely rejected the EMT6 re-challenge from Phase II were again inoculated/re-challenged (on Day 109) with 2×10⁶ EMT6 tumor cells (group 2) and monitored for 59 days. Age appropriate animals (N=5) were also inoculated for controls (group 1) at the same time.

From the final part of the study, it was observed that tumor uptake and growth were apparent three days after inoculation with mean tumor volumes of 101±14 and 69±6 for Groups 1 and 2 respectively. Animals given the second re-challenge were completely tumor free (complete rejection) 21 days after tumor cell implantation while all 5 of their age appropriate counterparts had a mean tumor volume of 1550±401 mm³. Animals in Group 2 remained tumor free until the end of the study (Day 168) and no significant body weight loss was observed.

This study demonstrates the efficacy of combining immune therapy using RSLAIL-2 and Anti-CTLA 4 in EMT6 murine mammary carcinoma tumors (Phase I) as well as durability and specificity of response, and the long term effect of the therapy in animals that respond well to treatment (Phase II and III). See FIG. 21 for a summary of the study from beginning to end and individual tumor growths for each phase.

Example 8

In Vivo Depletion Study

Assessing the Contribution of Cytotoxic Immune Cell Populations to Anti-Tumor Immunity Against EMT6 Murine Mammary Carcinoma Tumors after Effective Combined Immune Therapy with RSLAIL-2 and Anti-CTLA-4 or Anti-PD-1

The objective of this example was to assess the relative contribution of Natural Killer (NK) cells and CD8⁺ Cytotoxic T lymphocytes to antitumor efficacy when RSLAIL-2 is combined with immune checkpoint inhibition through antibody blockade of CTLA-4 or PD-1.

This study utilized 58 female BALB/c mice bearing EMT6 (Murine Mammary Carcinoma) tumors. Ten (10/58) animals were randomly selected and assigned to the vehicle control group (Days 0, 4, 8, i.p.). Eight (8/58) animals were assigned to the treatment group receiving a combination of anti-CTLA-4 i.p. (100 µg on Days 0, 4, and 8) and RSLAIL-2 i.v. (0.8 mg/kg on Day 4). Eight (8/58) animals were assigned to the CD8 depletion group, which in addition to the treatment of RSLAIL-2 and anti-CTLA-4, CD8 T cells were depleted by serial injection of rat anti-mouse CD8a (100 µg i.p. on Days −2, 0, 7). Eight (8/58) additional animals were assigned to the NK depletion group which in addition to the treatment of RSLAIL-2 and anti-CTLA-4, NK cells were depleted by serial injection of rabbit anti-bovine Asialo-GM1 (50 µl i.p. on Days −2, 0, 7).

Eight (8/58) animals were assigned to the treatment group receiving a combination of anti-PD-1 i.p. (100 µg on Days 0, 4, and 8) and RSLAIL-2 i.v. (0.8 mg/kg on Day 4). Eight (8/58) animals were assigned to the CD8 depletion group, which in addition to the treatment of RSLAIL-2 and anti-PD-1, CD8 T cells were depleted by serial injection of rat anti-mouse CD8a (100 µg i.p. on Days −2, 0, 7). Eight (8/58) additional animals were assigned to the NK depletion group which in addition to the treatment of RSLAIL-2 and anti-PD-1, NK cells were depleted by serial injection of rabbit anti-bovine Asialo-GM1 (50 µl i.p. on Days −2, 0, 7).

Treatment initiation (Day 0) was designated as seven days after inoculation of EMT6 cells at 2×10⁶ cells/site in 0.1 mL injection volumes, injected subcutaneously in the abdominal area, and the study was 11 days in duration. Tumor volumes (in mm³) and body weights (in grams) were measured 2 to 3 times a week. Table 8 presents the Initial and Mean Relative Tumor Volume for each group on Day 11. For combinations with RSLAIL-2 and Anti-CTLA-4, tumor volumes and body weights are presented in FIG. 22, while relative tumor volume and percent body weight change from Day 0 are presented in FIG. 23. For combinations with RSLAIL-2 and Anti-PD-1, tumor volumes and body weights are presented in FIG. 24, while relative tumor volume and percent body weight change from Day 0 are presented in FIG. 25.

The results of the study showed a Tumor Growth Inhibition (TGI) of 76.9% (p<0.05) in the RSLAIL-2 and Anti-CTLA-4 treatment group, calculated using Mean Relative Tumor Volumes between control animals (553%) and treated animals (128%) on Day 11 utilizing a one-way ANOVA and Tukey's multiple comparisons post-test (GraphPad Prism version 6.03 for Windows, GraphPad Software, San Diego Calif.).

When treatment of RSLAIL-2 and Anti-CTLA-4 was combined with serial injections of neutralizing CD8a antibodies, leading to in vivo depletion of cytotoxic CD8 T cells, the result was abrogation of treatment efficacy with a Mean Relative Tumor Volume of 520% and Tumor Growth Inhibition of 5.98% on Day 11 which did not reach statistical significance compared to the vehicle control.

with anti-Asialo-GM1 led to two animals found expired on Day 8 of the study in the group also receiving RSLAIL-2 and Anti-CTLA-4 and three animals found expired on Day 8 of the study in the group also receiving RSLAIL-2 and Anti-PD-1.

TABLE 8

Phase I Summary of Results (Mean ± SE)

| Treatment | Dose | N | Tumor Volume on Treatment Initiation (mm³) | Mean Relative Tumor Volume on Day 11 (%) | Mean Tumor Growth Inhibition[1] On Day 11 (%) | p value[2] |
|---|---|---|---|---|---|---|
| Vehicle Control (Day 0, 4, 8) | NA | 10 | 177 ± 10 | 553 ± 49 | NA | NA |
| RSLAIL-2 (Day 4) + Anti CTLA-4 (Day 0, 4, 8) | 0.8 mg/kg 100 µg | 8 | 198 ± 16 | 128 ± 24 | 76.9 | <0.05 |
| RSLAIL-2 (Day 4) + Anti CTLA-4 (Day 0, 4, 8) + anti-CD8a (Day −2, 0, 7) | 0.8 mg/kg 100 µg 100 µg | 8 | 195 ± 14 | 520 ± 46 | 5.98 | NS[3] |
| RSLAIL-2 (Day 4) + Anti CTLA-4 (Day 0, 4, 8) + Anti Asialo-GM1 (Day −2, 0, 7) | 0.8 mg/kg 100 µg 50 µl | 8 | 177 ± 13 | 483 ± 51 | 12.7 | NS |
| RSLAIL-2 (Day 4) + Anti PD-1 (Day 0, 4, 8) | 0.8 mg/kg 100 µg | 8 | 184 ± 10 | 285 ± 46 | 48.5 | <0.05 |
| RSLAIL-2 (Day 4) + Anti PD-1 (Day 0, 4, 8) + anti-CD8a (Day −2, 0, 7) | 0.8 mg/kg 100 µg 100 µg | 8 | 176 ± 10 | 539 ± 45 | 2.53 | NS |
| RSLAIL-2 (Day 4) + Anti PD-1 (Day 0, 4, 8) + Anti Asialo-GM1 (Day −2, 0, 7) | 0.8 mg/kg 100 µg 50 µl | 8 | 223 ± 15 | 364 ± 65 | 34.2 | NS |

[1]Mean tumor growth inhibition (% TGI) was assessed on Day 18 (last day control animals were present) by using the formula: % TGI = (1 − (Relative Tumor Volume (%)$^{Treatment\ Group}$ ÷ Relative Tumor Volume (%)$^{Control\ Group}$) × 100
[2]One-Way ANOVA with multiple comparisons, Tukey's post-test.
[3]NS, did not achieve statistical significance.

When treatment of RSLAIL-2 and Anti-CTLA-4 was combined with serial injections of neutralizing anti-Asialo-GM1 antibodies, leading to in vivo depletion of NK cells, the result was abrogation of treatment efficacy with a Mean Relative Tumor Volume of 483% and Tumor Growth Inhibition of 12.7% on Day 11 which did not reach statistical significance compared to the vehicle control.

When RSLAIL-2 was combined with Anti-PD-1, the Mean Relative Tumor Volume at Day 100 was 285% resulting in a Tumor Growth Inhibition (TGI) of 48.5% (p<0.05).

When treatment of RSLAIL-2 and PD-1 was combined with serial injections of neutralizing CD8a antibodies, the result was abrogation of treatment efficacy with a Mean Relative Tumor Volume of 539% and Tumor Growth Inhibition of 2.53% on Day 11 which did not reach statistical significance compared to the vehicle control.

When treatment of RSLAIL-2 and Anti-PD-1 was combined with serial injections of neutralizing anti-Asialo-GM1 antibodies, the result was abrogation of treatment efficacy with a Mean Relative Tumor Volume of 364% and Tumor Growth Inhibition of 34.2% on Day 11 which did not reach statistical significance compared to the vehicle control.

While no significant body weight loss was observed from RSLAIL-2 when combined with Anti-CTLA-4 or Anti-PD-1, or when the treatment was combined with the addition of CD8 or anti-Asialo-GM1 antibody ablation, combination This study demonstrates the efficacy of combining immune therapy using RSLAIL-2 and Anti-CTLA-4 or RSLAIL-2 and Anti-PD-1 in EMT6 murine mammary carcinoma tumors. In addition, the loss of antitumor efficacy following in vivo depletion of NK and CD8 T cells suggests a role for both cell types in this efficacy.

The invention claimed is:
1. A method of treating a patient suffering from a solid cancer, the method comprising:
(a) administering to the patient an effective, IL-2Rβ-activating amount of a long acting, interleukin-2 receptor beta (IL-2Rβ)-selective agonist of a formula:

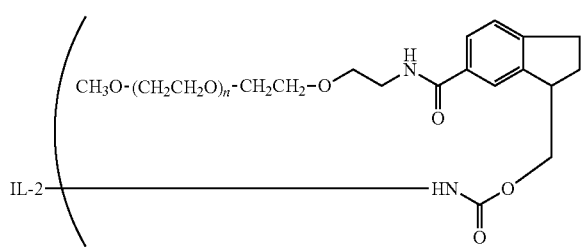

-continued

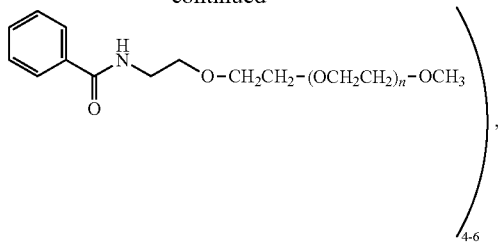

or a pharmaceutically acceptable salt form thereof, where IL-2 is interleukin-2, and n ranges from 3 to 4000; and (b) administering to the patient an effective, CTLA-4 pathway-inhibiting amount of an anti-CTLA-4 antibody, wherein step (a) is carried out after step (b); or administering to the patient an effective, PD-1 pathway-inhibiting amount of an anti-PD-1 antibody, wherein step (a) is carried out before, after or simultaneously with step (b).

2. The method of claim 1, wherein the patient is a human.

3. The method of claim 1, wherein administering steps (a) and (b) both comprise parenteral administering.

4. The method of claim 1, wherein the solid cancer is selected from the group consisting of breast cancer, ovarian cancer, colon cancer, colorectal cancer, gastric cancer, malignant melanoma, liver cancer, small cell lung cancer, non-small cell lung cancer, thyroid cancers, kidney cancer, cancer of the bile duct, brain cancer, cervical cancer, maxillary sinus cancer, bladder cancer, esophageal cancer, Hodgkin's disease and adrenocortical cancer.

5. The method of claim 1, wherein the cancer is colon cancer.

6. The method of claim 1, wherein the cancer is breast cancer.

7. The method of claim 1, wherein step (b) comprises administering to the patient an effective, PD-1 pathway-inhibiting amount of an anti-PD-1 antibody and step (a) is carried out prior to step (b).

8. The method of claim 1, wherein step (b) comprises administering to the patient an effective, PD-1 pathway-inhibiting amount of an anti-PD-1 antibody and step (a) is carried out after step (b).

9. The method of claim 1, wherein step (b) comprises administering to the patient an effective, PD-1 pathway-inhibiting amount of an anti-PD-1 antibody and steps (a) and (b) are carried out simultaneously.

10. The method of claim 1, wherein step (b) comprises administering to the patient an effective, CTLA-4 pathway-inhibiting amount of an anti-CTLA-4 antibody.

11. The method of claim 1, wherein step (b) comprises administering to the patient an effective, PD-1 pathway-inhibiting amount of an anti-PD-1 antibody.

12. The method of claim 1, wherein the long acting, IL-2Rβ-selective agonist is comprised in a composition that contains no more than about ten mole percent of compounds having a formula

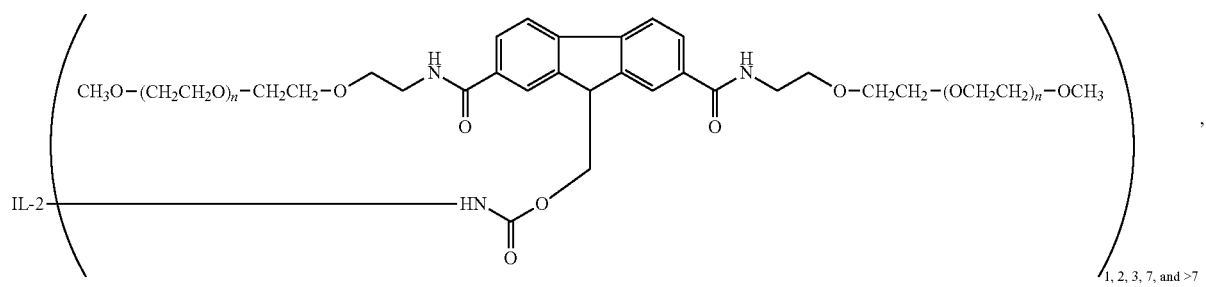

or a pharmaceutically acceptable salt thereof, where IL-2 is interleukin-2, and n ranges from 3 to 4000.

13. The method of claim 1, wherein each branched polyethylene glycol moiety comprised in the long acting, IL-2Rβ-selective agonist has a molecular weight of about 20 kilodaltons.

14. The method of claim 1, wherein the interleukin-2 is aldesleukin, and further wherein step (b) comprises administering to a human an effective PD-1 pathway-inhibiting amount of an anti-PD-1 antibody.

15. The method of claim 1, wherein the interleukin-2 is aldesleukin, and further wherein step (b) comprises administering to a human an effective, CTLA-4 pathway-inhibiting amount of an anti-CTLA-4 antibody, wherein step (a) is carried out after step (b).

* * * * *